(12) United States Patent
Marcireau et al.

(10) Patent No.: US 6,890,733 B1
(45) Date of Patent: May 10, 2005

(54) MEKK1 (SERINE THREONINE KINASES)-INTERACTING FHA (FORKHEAD ASSOCIATED DOMAIN) PROTEIN 1 (M1F1)

(75) Inventors: Christophe Marcireau, Paris (FR); Marie-Christine Multon, Versailles (FR); Valerie Polard-Housset, Jouy en Josas (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/744,125

(22) PCT Filed: Jul. 21, 1999

(86) PCT No.: PCT/EP99/05142

§ 371 (c)(1),
(2), (4) Date: Sep. 17, 2001

(87) PCT Pub. No.: WO00/05362

PCT Pub. Date: Feb. 3, 2000

Related U.S. Application Data

(60) Provisional application No. 60/093,590, filed on Jul. 21, 1998.

(51) Int. Cl.⁷ ............................. C12P 21/02; C12N 1/21; C12N 5/10; C12N 9/12; C07H 21/04
(52) U.S. Cl. .............. 435/69.1; 435/252.3; 435/254.11; 435/320.1; 435/325; 530/350; 536/23.5
(58) Field of Search ............................. 435/69.1, 252.3, 435/254.11, 320.1, 325; 530/350; 536/23.5

(56) References Cited

PUBLICATIONS

Ren et al. (Sep. 10, 1997) GenBank accession AF015308 (human).*
Ren et al. (Sep. 10, 1997) GenBank accession AF015309 (mouse).*
Bruni et al. Herpes Simplex Virus 1 Regulatory Protein ICP22 Interacts with a New Cell Cycle–Regulated Factor and accumulates in a Cell Cycle–Dependent Fashion in Infected Cells. J. Virol. 72(11):8525–8531, Nov. 1998.
Ren et al. "The 58–kDa microspherule protein (MSP58), a nucleolar protein, interacts with nucleolar protein p120" Eur. J. Biochem. 253(3):734–742 (May 1, 1998).

* cited by examiner

Primary Examiner—Elizabeth Slobodyansky

(57) ABSTRACT

The present invention relates to a novel protein of the MEKK signal transduction pathway, and the gene encoding it. The invention further relates to diagnostic and therapeutic uses of the protein or the gene, and to methods of screening for agonists or antagonists of the protein, particularly with respect to MEKK activity. In particular, the invention provides a gene encoding MIF1, the MIF1 protein, and antibodies that specifically bind MIF1. MIF1 and the MIF1 gene can be used in screening assays, particularly to identify agonists and antagonists of MIF1 interaction with MEKK, and thus modulators of the MEKK signal pathway. MIF1 gene (or cDNA) can also be delivered to cells, e.g., for in vitro screening or testing, or in vivo or ex vivo for gene therapy.

23 Claims, 13 Drawing Sheets

SEQUENCE LISTING

<160> NUMBER OF SEQ ID NOS: 16

<210> SEQ ID NO 1
<211> LENGTH: 1553
<212> TYPE: DNA
<213> ORGANISM: Homo sapiens

<400> SEQUENCE: 1
gaattcggca cgaggtgggg tggaaccagg gcgctgttcg gggagtgaac cctcctccag      60
tgagaaaaag aaggtatcca aagcccccag cactcctgtg ccacccagcc cagcccagc     120

```
ccctggactc accaagcgtg tgaagaagag taaacagcca cttcaggtga ccaaggatct    180
gggccgctgg aagcctgcaa atgacctcct gctcataaat gctgtgttgc agaccaacga    240
cctgacctcc gtccacctgg gcgtgaaatt cagctgccgc ttcacccttc gggaggtcca    300
ggagcgttgg tacgccctgc tctacgatcc tgtcatctcc aagttggcct gtcaggccat    360
gaggcagctg cacccagagg ctattgcagc catccagagc aaggccctgt ttagcaaggc    420
tgaggagcag ctgctgagca agtgggatc gaccagccag cccaccttgg agaccttcca    480
ggacctgctg cacagacacc ctgatgcctt ctacctggcc cgtaccgcga aggccctgca    540
ggcccactgg cagctcatga agcagtatta cctgctggag gaccagacag tgcagccgct    600
gcccaaaggg gaccaagtgc tgaacttctc tgatgcagag gacctgattg atgacagtaa    660
gctcaaggac atgcgagatg aggtcctgga acatgagctg atggtggctg accggcgcca    720
gaagcgagag attcggcagc tggaacagga actgcataag tggcaggtgc tagtggacag    780
catcacaggc atgagctctc cggacttcga caaccagaca ctggcagtgc tgcggggccg    840
catggtgcgg tacctgatgc gctcgcgtga gatcaccctg ggcagagcaa ccaaggataa    900
ccagattgat gtggacctgt ctctggaggg tccggcctgg aagatatccc ggaaacaagg    960
tgtcatcaag ctgaagaaca acggtgattt cttcattgcc aatgagggtc gacggcccat   1020
ctacatcgat ggacggccgg tgctctgtgg ctccaaatgg cgcctcagca acaactctgt   1080
ggtggagatc gccagcctgc gattcgtctt ccttatcaac caggacctca ttgccctcat   1140
cagggctgag gctgccaaga tcacaccaca gtgaggaatg gtggcaggac tcgtgggccc   1200
tctccggcct gtttcccctg ccactccagc ccccttgagc tgggaactca ggctcctgga   1260
aaaacctggg cagtgggagg ctcagctgcg ggccattgat ttgagccttt gagggaggat   1320
agggctggcc tttgtgaagc cagcagaggc tgagaacctc aggcttccct agatccagag   1380
ccctcccca tcttcctctc tctaaaaaca accctacccc ccattctacc cccattgcc   1440
accttcactc ctgtgtctcc agctgattag cctcagactc ttctttatt gttttttcttt   1500
tgtaaataaa aagcaccagg ttccaaagta aaaaaaaaaa aaaaaaactc gag          1553
```

<210> SEQ ID NO 2
<211> LENGTH: 390
<212> TYPE: PRT
<213> ORGANISM: Homo sapiens

<400> SEQUENCE: 2

```
Asn Ser Ala Arg Gly Gly Val Glu Pro Gly Arg Cys Ser Gly Ser Glu
1               5                   10                  15

Pro Ser Ser Ser Glu Lys Lys Lys Val Ser Lys Ala Pro Ser Thr Pro
            20                  25                  30

Val Pro Pro Ser Pro Ala Pro Ala Pro Gly Leu Thr Lys Arg Val Lys
        35                  40                  45

Lys Ser Lys Gln Pro Leu Gln Val Thr Lys Asp Leu Gly Arg Trp Lys
    50                  55                  60

Pro Ala Asn Asp Leu Leu Leu Ile Asn Ala Val Leu Gln Thr Asn Asp
65                  70                  75                  80

Leu Thr Ser Val His Leu Gly Val Lys Phe Ser Cys Arg Phe Thr Leu
                85                  90                  95

Arg Glu Val Gln Glu Arg Trp Tyr Ala Leu Leu Tyr Asp Pro Val Ile
            100                 105                 110

Ser Lys Leu Ala Cys Gln Ala Met Arg Gln Leu His Pro Glu Ala Ile
        115                 120                 125
```

```
Ala Ala Ile Gln Ser Lys Ala Leu Phe Ser Lys Ala Glu Glu Gln Leu
        130                 135                 140

Leu Ser Lys Val Gly Ser Thr Ser Gln Pro Thr Leu Glu Thr Phe Gln
145                 150                 155                 160

Asp Leu Leu His Arg His Pro Asp Ala Phe Tyr Leu Ala Arg Thr Ala
                165                 170                 175

Lys Ala Leu Gln Ala His Trp Gln Leu Met Lys Gln Tyr Tyr Leu Leu
            180                 185                 190

Glu Asp Gln Thr Val Gln Pro Leu Pro Lys Gly Asp Gln Val Leu Asn
        195                 200                 205

Phe Ser Asp Ala Glu Asp Leu Ile Asp Ser Lys Leu Lys Asp Met
210                 215                 220

Arg Asp Glu Val Leu Glu His Glu Leu Met Val Ala Asp Arg Gln
225                 230                 235                 240

Lys Arg Glu Ile Arg Gln Leu Glu Gln Glu Leu His Lys Trp Gln Val
            245                 250                 255

Leu Val Asp Ser Ile Thr Gly Met Ser Ser Pro Asp Phe Asp Asn Gln
        260                 265                 270

Thr Leu Ala Val Leu Arg Gly Arg Met Val Arg Tyr Leu Met Arg Ser
        275                 280                 285

Arg Glu Ile Thr Leu Gly Arg Ala Thr Lys Asp Asn Gln Ile Asp Val
        290                 295                 300

Asp Leu Ser Leu Glu Gly Pro Ala Trp Lys Ile Ser Arg Lys Gln Gly
305                 310                 315                 320

Val Ile Lys Leu Lys Asn Asn Gly Asp Phe Phe Ile Ala Asn Glu Gly
                325                 330                 335

Arg Arg Pro Ile Tyr Ile Asp Gly Arg Pro Val Leu Cys Gly Ser Lys
            340                 345                 350

Trp Arg Leu Ser Asn Asn Ser Val Val Glu Ile Ala Ser Leu Arg Phe
        355                 360                 365

Val Phe Leu Ile Asn Gln Asp Leu Ile Ala Leu Ile Arg Ala Glu Ala
370                 375                 380

Ala Lys Ile Thr Pro Gln
385                 390

<210> SEQ ID NO 3
<211> LENGTH: 669
<212> TYPE: DNA
<213> ORGANISM: Artificial
<220> FEATURE:
<223> OTHER INFORMATION: Sequence of the insert of the plasmid pCM524

<400> SEQUENCE: 3
gaattcggca cgagcattaa acttatacat gtattttagg tttctgctat ggcaggtatt      60
ttttgtttca agaacgaatt tctgttaaa taaagttata gtagctattg taacaaataa     120
atcctcaaat atgagtggtt taacatttat ataaagtgaa aaacataggt taccaattag     180
ctgggagctc tcatccaagt ggtgattcag taatccaggc tcctttcatt ttgtggctcc     240
tctatattca acatataact actgaagtca ttgctgacag cagcatggga aatcccagta     300 ggaattttt tatgggataa ccttggaagt attgcccaac acttcctcct aaattctatt     360
gttcagaaat cagacacaaa atctcactta agcaaggaag cctgaaaaat gtagtagaac     420
tgtgtgatta ggagaaagta atgggtttgg tgagtacgta ttagtatctc tcacattggg     480
agaaatggct ttttatatgt ttttaagaaa caaatttgt tatctttctc tccattggct      540
```

```
ccattgcccc agcaaagtag tagaacaaaa ataatatatt ttaaaattta acattatata      600
ttaatgataa tgcttaaaca gttgtattta cctgtttcaa aagaaaaaa aaaaaaaaa        660 aaactcgag                                                              669
```

```
<210> SEQ ID NO 4
<211> LENGTH: 128
<212> TYPE: PRT
<213> ORGANISM: Artificial
<220> FEATURE:
<223> OTHER INFORMATION: deduced amino acid sequence of the insert of
      the plasmid pCM524

<400> SEQUENCE: 4
```

```
Asn Ser Ala Arg Glu Arg Arg Gln Arg Glu Glu Arg Arg Gln Ser Asn
 1               5                  10                  15

Leu Gln Glu Val Leu Glu Arg Glu Arg Arg Glu Leu Glu Lys Leu Tyr
            20                  25                  30

Gln Glu Arg Lys Met Ile Glu Glu Ser Leu Lys Ile Lys Ile Lys Lys
        35                  40                  45

Glu Leu Glu Met Glu Asn Glu Leu Glu Met Ser Asn Gln Glu Ile Lys
 50                  55                  60

Asp Lys Ser Ala His Ser Glu Asn Pro Leu Glu Lys Tyr Met Lys Ile
 65                  70                  75                  80

Ile Gln Gln Glu Gln Asp Gln Glu Ser Ala Asp Lys Ser Ser Lys Lys
                85                  90                  95

Met Val Gln Glu Gly Ser Leu Val Asp Thr Leu Gln Ser Ser Asp Lys
            100                 105                 110

Val Glu Ser Leu Thr Gly Phe Ser His Glu Glu Leu Asp Asp Ser Trp
        115                 120                 125
```

```
<210> SEQ ID NO 5
<211> LENGTH: 669
<212> TYPE: DNA
<213> ORGANISM: Artificial
<220> FEATURE:
<223> OTHER INFORMATION: Insert of plasmid pCM482

<400> SEQUENCE: 5
gaattcggca cgagcattaa acttatacat gtattttagg tttctgctat ggcaggtatt      60
ttttgtttca agaacgaatt ttctgttaaa taaagttata gtagctattg taacaaataa     120
atcctcaaat atgagtggtt taacatttat ataagtgaa aaacataggt taccaattag      180 ctggagctc tcatccaagt ggtgattcag taatccaggc tcctttcatt ttgtggctcc      240
tctatattca acatataact actgaagtca ttgctgacag cagcatggga aatcccagta     300 ggaattttt tatgggataa ccttggaagt attgcccaac acttcctcct aaattctatt     360
gttcagaaat cagacacaaa atctcactta agcaaggaag cctgaaaaat gtagtagaac     420
tgtgtgatta ggagaaagta atgggtttgg tgagtacgta ttagtatctc tcacattggg     480
agaaatggct ttttatatgt ttttaagaaa caaattttgt tatctttctc tccattggct     540
ccattgcccc agcaaagtag tagaacaaaa ataatatatt ttaaaattta acattatata     600
ttaatgataa tgcttaaaca gttgtattta cctgtttcaa aagaaaaaa aaaaaaaaa      660 aaactcgag                                                              669
```

```
<210> SEQ ID NO 6
<211> LENGTH: 50
```

-continued

```
<212> TYPE: PRT
<213> ORGANISM: Artificial
<220> FEATURE:
<223> OTHER INFORMATION: Deduced amino acid sequence of insert of
      plasmid pCM482

<400> SEQUENCE: 6

Asn Ser Ala Arg Ala Leu Asn Leu Tyr Met Tyr Phe Arg Phe Leu Leu
1               5                   10                  15

Trp Gln Val Phe Phe Val Ser Lys Asn Glu Phe Leu Leu Asn Lys Val
            20                  25                  30

Ile Val Ala Ile Val Thr Asn Lys Ser Ser Asn Met Ser Gly Leu Thr
        35                  40                  45

Phe Ile
    50

<210> SEQ ID NO 7
<211> LENGTH: 1914
<212> TYPE: DNA
<213> ORGANISM: Murinae gen. sp.

<400> SEQUENCE: 7
cgcggagaaa ttgttggatc tggcagtcta ggaatgaatc tcctctcagc ctttaagctc      60
acctggtcag atccttgga tgagcctgtg ggaccgttcc tcctagcccg gtggtttgga     120
accagtggct ttgggactgt aagaggatgg acaaagattc tcagggctg ctagattcat    180
ccctgatggc atcaggcact gccagccgct cagaggatga ggagtcactg gcagggcaga     240
agcgagcctc ctcccaggcc ttgggcacca tccctaaacg gagaagctcc tccaggttca     300
tcaagaggaa gaagttcgat gatgagctgg tggagagcag cctggcaaaa tcttctaccc     360
gggcaaaggg ggccagtggg gtggaaccag gcgctgttc ggggagtgaa ccctcctcca     420
gtgagaagaa gaaggtatcc aaagccccca gcactcctgt gccacccagc ccagccccag     480
cccctggact caccaagcgt gtgaagaaga gtaaacagcc acttcaggtg accaaggatc     540
tgggccgctg gaagcctgca gatgacctcc tgctcataaa tgctgtgttg cagaccaacg     600
acctgacctc cgtccacctg ggcgtgaaat tcagctgccg cttcacccct cgggaggtcc     660
aggagcgttg gtacgccctg ctctacgatc ctgtcatctc caagttggcc tgtcaggcca     720
tgaggcagct gcacccagag gctattgcag ccatccagag caaggccctg tttagcaagg     780
ctgaggagca gctgctgagc aaagtgggat cgaccagcca gcccaccttg gagaccttcc     840
aggacctgct gcacagacac cctgatgcct tctacctggc ccgtaccgcg aaggccctgc     900
aggcccactg gcagctcatg aagcagtatt acctgctgga ggaccagaca gtgcagccgc     960
tgcccaaagg ggaccaagtg ctgaacttct ctgatgcaga ggacctgatt gatgacagta    1020
agctcaagga catgcgagat gaggtcctgg aacatgagct gatggtggct gaccggcgcc    1080
agaagcgaga gattcggcag ctggaacagg aactgcataa gtggcaggtg ctagtggaca    1140
gcatcacagg catgagctct ccggacttcg acaaccagac actggcagtg ctgcggggcc    1200
gcatggtgcg gtacctgatg cgctcgcgtg agatcaccct gggcagagca accaaggata    1260
accagattga tgtggacctg tctctggagg tccggcctg aagatatcc cggaaacaag    1320
gtgtcatcaa gctgaagaac aacggtgatt tcttcattgc caatgagggt cgacggccca    1380
tctacatcga tggacggccg gtgctctgtg ctccaaatg gcgcctcagc aacaactctg    1440
tggtggagat cgccagcctg cgattcgtct tcctatcaa ccaggacctc attgccctca    1500
tcagggctga ggctgccaag atcacaccac agtgaggaat ggtggcagga ctcgtgggcc    1560
```

```
ctctccggcc tgtttcccct gccactccag cccccttgag ctgggaactc aggctcctgg    1620
aaaaacctgg gcagtgggag gctcagctgc gggccattga tttgagcctt tgagggagga    1680
tagggctggc ctttgtgaag ccagcagagg ctgagaacct caggcttccc tagatccaga    1740
gcccctcccc atcttcctct ctctaaaaac aaccctaccc cccattctac cccccattgc    1800
caccttcact cctgtgtctc cagctgatta gcctcagact cttcttttat tgttttcttt    1860
ttgtaaataa aaagcaccag gttccaaagt aaaaaaaaaa aaaaaaaact cgag          1914
```

<210> SEQ ID NO 8
<211> LENGTH: 462
<212> TYPE: PRT
<213> ORGANISM: Murinae gen. sp.

<400> SEQUENCE: 8

```
Met Asp Lys Asp Ser Gln Gly Leu Leu Asp Ser Ser Leu Met Ala Ser
1               5                  10                  15

Gly Thr Ala Ser Arg Ser Glu Asp Glu Glu Ser Leu Ala Gly Gln Lys
            20                  25                  30

Arg Ala Ser Ser Gln Ala Leu Gly Thr Ile Pro Lys Arg Arg Ser Ser
        35                  40                  45

Ser Arg Phe Ile Lys Arg Lys Phe Asp Asp Glu Leu Val Glu Ser
    50                  55                  60

Ser Leu Ala Lys Ser Ser Thr Arg Ala Lys Gly Ala Ser Gly Val Glu
65                  70                  75                  80

Pro Gly Arg Cys Ser Gly Ser Glu Pro Ser Ser Glu Lys Lys Lys
                85                  90                  95

Val Ser Lys Ala Pro Ser Thr Pro Val Pro Pro Ser Ala Pro Ala
            100                 105                 110

Pro Gly Leu Thr Lys Arg Val Lys Lys Ser Lys Gln Pro Leu Gln Val
        115                 120                 125

Thr Lys Asp Leu Gly Arg Trp Lys Pro Ala Asp Asp Leu Leu Leu Ile
    130                 135                 140

Asn Ala Val Leu Gln Thr Asn Asp Leu Thr Ser Val His Leu Gly Val
145                 150                 155                 160

Lys Phe Ser Cys Arg Phe Thr Leu Arg Glu Val Gln Glu Arg Trp Tyr
                165                 170                 175

Ala Leu Leu Tyr Asp Pro Val Ile Ser Lys Leu Ala Cys Gln Ala Met
            180                 185                 190

Arg Gln Leu His Pro Glu Ala Ile Ala Ile Gln Ser Lys Ala Leu
        195                 200                 205

Phe Ser Lys Ala Glu Gln Leu Leu Ser Lys Val Gly Ser Thr Ser
    210                 215                 220

Gln Pro Thr Leu Glu Thr Phe Gln Asp Leu Leu His Arg His Pro Asp
225                 230                 235                 240

Ala Phe Tyr Leu Ala Arg Thr Ala Lys Ala Leu Gln Ala His Trp Gln
                245                 250                 255

Leu Met Lys Gln Tyr Tyr Leu Leu Glu Asp Gln Thr Val Gln Pro Leu
            260                 265                 270

Pro Lys Gly Asp Gln Val Leu Asn Phe Ser Asp Ala Glu Asp Leu Ile
        275                 280                 285

Asp Asp Ser Lys Leu Lys Asp Met Arg Asp Glu Val Leu Glu His Glu
    290                 295                 300

Leu Met Val Ala Asp Arg Arg Gln Lys Arg Glu Ile Arg Gln Leu Glu
```

```
305                 310                 315                 320
Gln Glu Leu His Lys Trp Gln Val Leu Val Asp Ser Ile Thr Gly Met
                325                 330                 335
Ser Ser Pro Asp Phe Asp Asn Gln Thr Leu Ala Val Leu Arg Gly Arg
                340                 345                 350
Met Val Arg Tyr Leu Met Arg Ser Arg Glu Ile Thr Leu Gly Arg Ala
                355                 360                 365
Thr Lys Asp Asn Gln Ile Asp Val Asp Leu Ser Leu Glu Gly Pro Ala
                370                 375                 380
Trp Lys Ile Ser Arg Lys Gln Gly Val Ile Lys Leu Lys Asn Asn Gly
385                 390                 395                 400
Asp Phe Phe Ile Ala Asn Glu Gly Arg Arg Pro Ile Tyr Ile Asp Gly
                405                 410                 415
Arg Pro Val Leu Cys Gly Ser Lys Trp Arg Leu Ser Asn Asn Ser Val
                420                 425                 430
Val Glu Ile Ala Ser Leu Arg Phe Val Phe Leu Ile Asn Gln Asp Leu
                435                 440                 445
Ile Ala Leu Ile Arg Ala Glu Ala Ala Lys Ile Thr Pro Gln
                450                 455                 460

<210> SEQ ID NO 9
<211> LENGTH: 23
<212> TYPE: DNA
<213> ORGANISM: Artificial
<220> FEATURE:
<223> OTHER INFORMATION: primer

<400> SEQUENCE: 9
ctattcgatg atgaagatac ccc                                       23

<210> SEQ ID NO 10
<211> LENGTH: 18
<212> TYPE: DNA
<213> ORGANISM: Artificial
<220> FEATURE:
<223> OTHER INFORMATION: Primer

<400> SEQUENCE: 10
cgcggagaaa ttgttgga                                             18

<210> SEQ ID NO 11
<211> LENGTH: 26
<212> TYPE: DNA
<213> ORGANISM: Artificial
<220> FEATURE:
<223> OTHER INFORMATION: primer

<400> SEQUENCE: 11
ccgatatcgc acttggtccc ctttgg                                    26

<210> SEQ ID NO 12
<211> LENGTH: 56
<212> TYPE: DNA
<213> ORGANISM: Artificial
<220> FEATURE:
<223> OTHER INFORMATION: Primer

<400> SEQUENCE: 12
agcttccacc atggagcaga agctgatctc cgaggaggac ctggaattct ctcgag   56

<210> SEQ ID NO 13
```

-continued

```
<211> LENGTH: 56
<212> TYPE: DNA
<213> ORGANISM: Artificial
<220> FEATURE:
<223> OTHER INFORMATION: primer

<400> SEQUENCE: 13
gatcctcgag agaattccag gtcctcctcg gagatcagct tctgctccat ggtgga         56

<210> SEQ ID NO 14
<211> LENGTH: 26
<212> TYPE: DNA
<213> ORGANISM: Artificial
<220> FEATURE:
<223> OTHER INFORMATION: primer

<400> SEQUENCE: 14
cgggatccat ggacaaagat tctcag                                         26

<210> SEQ ID NO 15
<211> LENGTH: 53
<212> TYPE: DNA
<213> ORGANISM: Artificial
<220> FEATURE:
<223> OTHER INFORMATION: primer

<400> SEQUENCE: 15
agcttccacc atgtatccgt atgatgtgcc tgactacgca gaattctctc gag           53

<210> SEQ ID NO 16
<211> LENGTH: 53
<212> TYPE: DNA
<213> ORGANISM: Artificial
<220> FEATURE:
<223> OTHER INFORMATION: Primer

<400> SEQUENCE: 16
gatcctcgag agaattctgc gtagtcaggc acatcatacg gatacagggt gga           53
```

US 6,890,733 B1

MEKK1 (SERINE THREONINE KINASES)-INTERACTING FHA (FORKHEAD ASSOCIATED DOMAIN) PROTEIN 1 (M1F1)

CROSS REFERENCE TO RELATED APPLICATIONS

This application is a 371 filing of PCT/EP99/05142 which has an international filing date of Jul. 21, 1999 and which also claims the benefit of U.S. Provisional Application No. 60/093,590 filed Jul. 21, 1998.

FIELD OF THE INVENTION

The present invention relates to a novel protein of the MEKK signal transduction pathway, and the gene encoding it. The invention further relates to diagnostic and therapeutic uses of the protein or the gene, and to methods of screening for agonists or antagonists of the protein, particularly with respect to MEKK activity.

BACKGROUND OF THE INVENTION

The Mitogen-Activated Protein kinases (MAPs) have been recently the focus of intensive study. This family of homologous kinases is involved in a variety of cellular responses to extracellular stimuli and their respective activation status appears to be determinant for the cellular fate. The identification of distinct MAPK cascades, consisting in at least 3-kinase modules, well conserved between all eukaryotes, has partly enlighted the respective panel of responses involving each of the kinase signaling pathway. The ERKs module is activated by a mitogen or a differentiation signal and in turn, activates their substrates that include p90 ribosomal S6 kinase, cPLA2, PHAS-1, c-myc, MAPKAPK2 and Elk 1. On another hand, cellular responses to stresses, to some growth factors, pro-inflammatory cytokines, UV or γ-radiation, ceramides, vasoactive peptides, protein synthesis inhibitors or heat shock involve the activation of the Jun N-terminal Kinases (JNKs) and of the p38s/HOG. The end points of this stress kinase cascades are the phosphorylation of the c-Jun, Elk1 or ATF-2 (CRE-BP1) transcription factors. The persistent activation of the JNKs is associated with growth arrest, occurrence of apoptosis or activation of the hematopoietic cells.

The JNKs are activated by dual phosphorylation by the JNK kinases (MKK4/SEK1) which are, in turn, activated by upstream serine threonine kinases referred to as MEK kinases (MEKKs). MEKKs represent an expanding family of kinases. Mammalian MEKK1 cDNA encodes a protein of 78 kDa but several forms of MEKK1 were reported in various cell lines (50, 78 or 98 kDa). Thereafter, a rat MEKK1 full-length cDNA was cloned, encoding a 195 kDa protein. This was reported to be cleaved by a caspase, resulting in the expression of a shorter and more active kinase during anoikis (apoptosis due to cell detachment). The 98 kDa cleavage product corresponds to the 625 aminoacids at he C-terminal part of the full-length MEKK1. Recent datas have demonstrated that MEKK1 regulates also the nFκB transcription factor, by phosphorylating the iκb-α kinase.

The wide range of extracellular or intracellular stimuli leading to activation of the MAPKs raises the question of the specificity of their mechanism of activation. The activation steps of the mitogen kinase cascade (ERKs) have been described. In contrast, the first activating steps that regulate the stress kinase cascade are at the moment unknown. Common regulators of this MAPK/JNK cascade have been identified, such as phosphatases, and act as determinants of the balance between cellular growth and apoptosis, balance that regulates the homeostasis of all tissues.

Both Raf (the MAPKKK that is activated by mitogenic, Ras-dependent signals) and MEKK1 interact with GTP-bound Ras through its effector domain but there is no evidence that Ras-GTP activates directly the MEKK1 protein. Nevertheless, oncogenic Ras activates also the JNK cascade, and this activation seems to be necessary for Ras transformation.

These examples illustrate that MEKK1 participates to the regulation of a wide range of cellular events leading either to cell division, to cell activation or to cell death. Thus, a striking control of its activity should exist in the cells. An increase of MEKK1 activity could lead to an excess of apoptosis or T cell activation, and be at the origin of a wide range of pathologies as inflammation and asthma, immunosuppression, cardiac ischemia or hypertrophy, myelodysplasic syndromes, neurodegenerescence etc. On the other hand, a down-regulation of the MEKK1 activity could induce an excess of cell proliferation and/or survival and therefore lead to tumor growth, excessive angiogenesis, rheumatoid arthritis, psoriasis and sustained viral infections.

A cDNA that is 100% homologous to the MIF1 cDNA disclosed herein was published by Ren Y et al., Eur. J. Biochem., 253, pp734–742, 1998, acc Genbank AF015308, and, named *Homo sapiens* microspherule protein (MSP58). No function was assigned to this protein, however.

However, there is a need in the art to better understand the molecular mechanisms of MEKK-mediated cellular processes. In particular, there is a need in the art to identify a MEKK regulatory protein.

The present invention addresses this need, as discussed below.

The citation of any reference herein should not be construed as an admission that such reference is available as "Prior Art" to the instant application.

SUMMARY OF THE INVENTION

As noted above, the present invention concerns identification of an MEKK regulatory factor. The factor, termed herein MEKK interacting FHA protein (MIF1), provides an avenue for modulating MEKK activity, and thus many physiological processes such as apoptosis and cellular responses to inflammation and other stimuli.

Thus, in a first aspect, the present invention provides an isolated nucleic acid encoding an MEKK interacting FHA protein (MIF1), wherein the nucleic acid has a property selected from the following: it can be amplified by polymerase chain reaction (PCR) using an oligonucleotide primer derived from SEQ ID NO:1 or SEQ ID NO:7; it hybridizes under stringent conditions with a nucleic acid having a nucleotide sequence as depicted in SEQ ID NO:1; it encodes a polypeptide having an amino acid sequence selected from the group consisting of SEQ ID NO:2, SEQ ID NO:8, splice variants thereof, and allelic variants thereof, and it encodes a polypeptide which specifically binds to an antibody generated against a peptide corresponding to amino acids 16–28 of MIF1 as depicted in SEQ ID NO:8. In a specific embodiment, exemplified infra, the MIF1 has an amino acid sequence as depicted in SEQ ID NO:2, e.g.; the isolated nucleic acid comprises a nucleotide sequence as depicted in SEQ ID NO:1. In a further embodiment, exemplified infra, the MIF1 has an amino acid sequence as depicted in SEQ ID NO:8, e.g. the isolated nucleic acid comprises a nucleotide sequence as depicted in SEQ ID NO:7. In another embodiment, MIF1 has about 483 amino acids. In a specific embodiment, the term "about" or "approximately" means within 20%, preferably within 10%, and more preferably within 5% of a given value or range.

As can be readily appreciated by one of ordinary skill in the art, one effective way to prepare a nucleic acid of the invention, particularly a cDNA, is to amplify the nucleic acid from a cDNA library comprising a coding sequence for MIF1 using PCR. Various PCR primers, corresponding to any desired segment from SEQ ID NO:1 or SEQ ID NO:7 can be used in accordance with the invention. In specific embodiments, infra, PCR primers having the sequences depicted in SEQ ID NOS: 10, 11, and 14 were used to amplify and isolate a nucleic acid of the invention. Alternatively, a nucleic acid of the invention can be isolated or identified with an oligonucleotide probe, e.g., of at least 10 bases, which hybridizes under stringent conditions to a nucleotide having the sequence or the complementary sequence depicted in SEQ ID NO:7. In a specific aspect, the oligonucleotide can be used in a method for detecting genomic DNA (Southern analysis) or expression of mRNA (Northern analysis) encoding MIF1 in a cell. In either case, the method comprises contacting a sample from the cell with the oligonucleotide which is detectable, e.g., by labeling with a radioisotope or a chromophore or fluorophore, and detecting hybridization of the oligonucleotide with genomic DNA or mRNA in the sample, wherein detection of hybridization of the oligonucleotide with genomic DNA indicates the presence of a gene encoding MIF1 in the genome, and detection of hybridization with mRNA indicates expression of mRNA encoding MIF1. It is also possible to use quantitative methods, e.g. to detect the number of MIF1 genes in the genome, or to detect an increase or decrease in the level of expression of mRNA.

An oligonucleotide of the invention can also be an antisense oligonucleotide, i.e., one that binds to mRNA encoding MIF1 and prevents its translation in the cell. Such an antisense molecule can be encoded by a vector expressed in the cell, or can be a synthetic oligonucleotide, preferably one that includes non-phosphoester bonds so that it is resistant to intracellular nucleases.

In another embodiment, the isolated nucleic acid further comprising a sequence encoding a polypeptide tag, whereby the nucleic acid encodes a chimeric tagged MIF1 protein. Appropriate tags include, but are by no means limited to, a portion of Myc protein, a polyhistidine sequence, or a glutathione transferase protein.

Naturally, the nucleic acids of the invention, particularly cDNA molecules, can be provided in a cloning vector or in an expression vector. In an expression vector, the sequence coding for MIF1 is operatively associated with an expression control sequence permitting expression of MIF1 polypeptide in an expression competent host cell. Vectors of the invention include an RNA molecule, a plasmid DNA molecule, and a viral vector. When the vector is a plasmid DNA molecule, the plasmid DNA can further comprise a composition selected from the group consisting of a DNA condensing protein, a cationic lipid, a liposome, a polymer, and a DNA precipitating agent. When the vector is a viral vector, the viral vector can be a retrovirus, adenovirus, adeno-associated virus, herpes virus, and vaccinia virus, to name but a few such vectors. Preferred retrovirus vectors include vectors of the *lentivirus* family, such as HIV. In addition, the invention provides a host cell transfected with the cloning vector (such host cells will usually be prokaryotic cells, as exemplified infra) or expression vector. Host cells containing the expression vector include bacterial cells, yeast cells, and mammalian cells. In specific embodiments, both yeast cells and host cells are used.

The host cells of the invention can be used to produce MIF1 recombinantly. This method comprises culturing the host cell in culture medium under conditions permitting expression of MIF1; and isolating the MIF1 from the culture.

In another aspect, the invention provides an isolated MEKK interacting FHA protein (MIF1). The protein can be encoded by a nucleic acid of the invention. Alternatively, a MIF1 protein has an amino acid sequence selected from the group consisting of SEQ ID NO:2, SEQ ID NO:8, splice variants thereof, and allelic variants thereof. In yet another embodiment, the protein is characterized by specifically binding to an antibody generated against a peptide corresponding to amino acids 16–28 of MIF1 as depicted in SEQ ID NO:8. The invention provides both murine and human MIF1. In still another embodiment, the protein is a chimeric MIF1 comprising a polypeptide tag, e.g., as described above.

Also provided is an antigenic peptide which is a fragment of an isolated MEKK interacting FHA protein (MIF1). In a specific embodiment, the antigenic peptide has an amino acid sequence corresponding to amino acids 16–28 of SEQ ID NO:8.

Naturally, the invention further provides an antibody which specifically binds an MIF1 protein. Such antibodies can be used diagnostically, to detect the presence and optionally the quantity of MIF1 in cells. Antibodies of the invention, particularly single chain Fv antibodies (scFv) can also be used therapeutically, to suppress MIF1 activity. In a specific embodiment, exemplified infra, the antibody specifically recognizes MIF1 amino acids 16–28 of SEQ ID NO:8. In another specific embodiment, exemplified infra, the antibody is polyclonal. Monoclonal antibodies, and antibody fragments (in addition to scFv antibodies) are also contemplated by this invention. Using the antibody of the invention, one can detect expression of MIF1 protein in a cell by contacting a sample from the cell with the antibody under conditions permitting binding of the antibody to an MIF1 protein in the sample, and detecting binding of the antibody to a protein in the sample, wherein detection of binding of the antibody to the protein indicates expression of MIF1 in the cell. Using quantitative immunoassay or Western blotting methods, it is possible to quantitate the amount of MIF1, and particularly to detect increases or decreases in the amount of MIF1 relative to the cell at an earlier time, or to normal cells.

As noted above, MIF1 regulates the activity of MEKK. MEKK is an important signal transduction molecule in a number of systems. The present invention advantageously provides a method of screening for molecules that modulate the activity of MIF1, and thus MEKK. Any of the screening methods in the art can be used, particularly high throughput screening. In a specific embodiment, the method comprises contacting an MIF1 protein with a candidate molecule, and detecting binding of the molecule to the MIF1 protein. In a specific embodiment, detection of the binding of the molecule to MIF1 comprises detecting modulation of the interaction of MIF1 and MEKK. In a specific embodiment, modulation of the interaction of MIF1 and MEKK comprises detecting a change in the level of expression of a reporter gene expressed under control of a chimeric protein consisting of the MIF1 binding domain of MEKK and a DNA binding domain of a transcription activator in a cell line transfected with MIF1 and the MEKK chimeric protein.

More particularly, detection of expression is in transiently transfected mammalian cells. Transient modulation of MEKK activity is exemplified in the examples, infra. Screening methods of the invention permit identification of an MIF1 agonist or antagonist.

In yet a further embodiment, the invention provides a method of decreasing MEKK activity in a cell comprising increasing the level of MIF1 protein in the cell. The MIF1 protein can be a murine MIF1, and more preferably is a human MIF1. In a preferred embodiment, the cell has been transfected with a vector encoding MIF1 under conditions permitting expression of the MIF1 protein.

Alternatively, where desired, the invention provides a method of increasing MEKK activity in a cell comprising decreasing the level of MIF1 protein in the cell. The level of MIF1 protein can be decreased by introducing an MIF1 antisense nucleic acid into the cell, which antisense nucleic acid hybridizes under intracellular conditions to an MIF1 mRNA. Alternatively, the level of MIF1 protein can be decreased by introducing an a single chain Fv antibody (scFv) that specifically binds MIF1 into the cell at a level sufficient to bind to and inactivate MIF1.

A first object of the invention, then, is to provide a factor that regulates the activity of MEKK, specifically MEKK1.

A related object is to provide a nucleic acid encoding such a polypeptide.

Still a further object is to provide oligonucleotides, either as PCR primers to amplify a nucleic acid encoding the MEKK regulatory factor, or as hybridization probes to detect or isolate such a nucleic acid.

Yet another object of the invention is to provide for high level expression of the MEKK regulatory protein, either by fermentation of transfected or transduced cells to recover purified protein, or in vivo in cells for further testing in, vitro or for regulation of MEKK activity in vivo, e.g., for gene therapy.

A particular object of the invention is to provide for screening of small molecule modulators, e.g., agonists and antagonists, of MIF1 activity, particularly of MIF1 interaction with MEKK.

These and other objects are addressed by this invention, which is explained in greater detail in the attached drawings and the following Detailed Description and Examples.

DETAILED DESCRIPTION OF THE INVENTION

Figure 1:
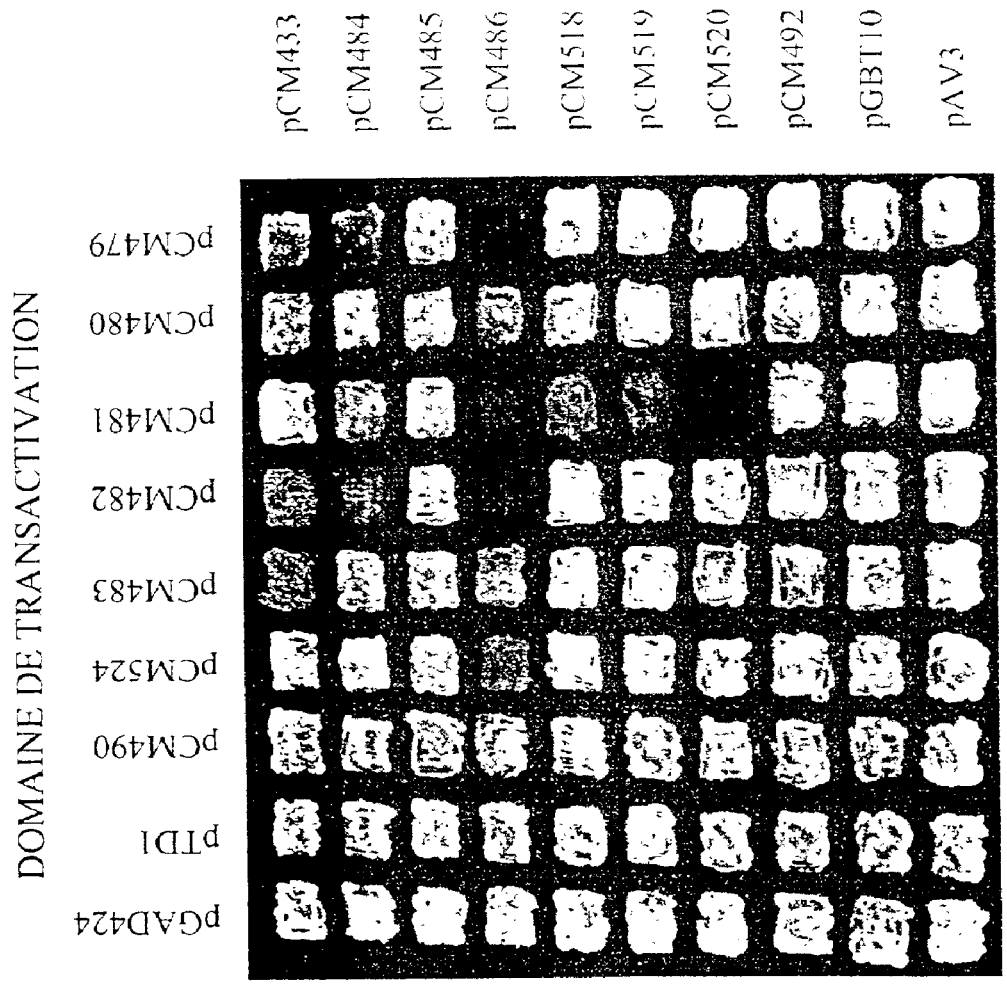
FIG. 1. Detection of β-GALACTOSIDASE activity in yeast strain γCM17 transformed by different plasmid pairs encoding truncated MEKK1 and partial or full length MIF1.

Because little is known about the upstream regulation of MEKK1, efforts were made to identify partners of MEKK1 in order to find putative regulators of its activity. The invention is based, in part, on the identification of such a regulatory protein, termed herein MIF1. Better knowledge of the activation and regulation pathways for MEKK1 could be afforded by the MIF1 protein. MIF1 (MEKK1-interacting FHA protein 1,483 amino acids) was cloned using a 2-hybrid strategy and MEKK1 as a bait.

MIF1 protein contains a protein motif identified in Prosite data banks. —This domain, the Forkhead Associated (FHA) domain has been described as involved in protein—protein interactions and could be a binding motif to phosphorylated serines and threonines. The only forkhead homologous protein probably located in the cytoplasm that was previously described is KAPP, a phosphatase interacting with a serine/threonine kinase in a phosphorylation-dependent manner.

The mapping of the interaction domain between MIF1 and MEKK1 indicated that the interaction between MIF1 and MEKK1 is MEKK1-phosphorylation dependent. The interaction in yeast, between MIF1 and MEKK1 can be observed only if MEKK1 has an unmodified kinase activity and autophosphorylates the site of interaction. The MEKK1 domain interacting with MIF1 was mapped in the regulatory domain of the kinase, between the amino acids 284–369, by using different fragments of the MEKK1 cDNA (2-hybrid) (see FIG. 1).

The invention accordingly relates to the use of the human cDNA encoding for the MIF1 protein, homologs, splicing variants, single point or deletion mutants and the proteins encoded by these sequences for their use in screening for small molecules or natural products, e.g., for inhibition of MEKKs/MIF1 interactions. Use of a 2-hybrid strain described in the examples, activation of MEKKs by phosphorylation, modification of MIF1 described activities, can be used in this process.

MIF1 can also be used in gene therapy applications (both coding and antisense molecules can be of use) in order to modify JNKs activation in cells. The pathologies concerned by these gene therapies based on MIF1 over-expression or down-regulation are discussed in the Background of the Invention, supra.

In addition, anti-MIF antibodies can be used in diagnostic and purification applications.

MIF1 cDNA and derivatives can be effectively used in a yeast 3-hybrid screening in order to clone a new MAP4K, as a regulator of MAP3K activities. MIF1 cDNA and derivatives can also be, used to screen for inhibitors of MAP4K.

These and other aspects of the invention, particularly isolation of MIF1 genes, expression of MIF1 protein, generation of anti-MIF1 antibodies, screening assays for modulation of MIF1, screening assays for identifying antagonists or agonists of MIF1/MEKK interaction, and delivery of MIF1 encoding vectors, in particular for gene therapy applications, are discussed in detail in the following sections. Section headers are provided merely for the reader's convenience, and are not to be deemed limiting in any respect.

Genes Encoding MIF1 Proteins

The present invention contemplates isolation of a gene encoding a MIF1 of the invention, including a full length, or naturally occurring form of MIF1, and any antigenic fragments thereof from any animal, particularly mammalian or avian, and more particularly human, source. As used herein, the term "gene" refers to an assembly of nucleotides that encode a polypeptide, and includes cDNA and genomic DNA nucleic acids. As used herein, "MIF1" refers to MIF1 polypeptide, and "MIF1" refers to a gene encoding MIF1 polypeptide.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"), *DNA Cloning: A Practical Approach*, Volumes I and II (D. N. Glover ed. 1985); *Oligonucleotide Synthesis*(M. J. Gait ed. 1984); *Nucleic Acid Hybridization* [B. D. Hames & S. J. Higgins eds. (1985)]; *Transcription And Translation*[B. D. Hames & S. J. Higgins, eds. (1984)]; *Animal Cell Culture*[R. I. Freshney, ed. (1986)]; *Immobilized Cells And Enzymes*[IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "cloning vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. Cloning vectors may be capable of replication in one cell type, and expression in another ("shuttle vector").

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecule s"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra. 9.50–0.51). For hybridization with shorter nucleic acids. i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

As used herein, the term "oligonucleotide" refers to a nucleic acid, generally of at least 18 nucleotides, that is hybridizable to a genomic DNA molecule, a cDNA molecule, or an mRNA molecule encoding MIF1. Oligonucleotides can be labeled, e.g., with $^{32}$P-nucleotides or nucleotides to which a label, such as biotin, has been covalently conjugated (see the discussion, supra, with respect to labeling MIF1 polypeptides). In one embodiment, a labeled oligonucleotide can be used as a probe to detect the presence of a nucleic acid encoding MIF1. In another embodiment, oligonucleotides (one or both of which may be labeled) can be used as PCR primers, either for cloning full length or a fragment of MIF1, or to detect the presence of nucleic acids encoding MIF1. In a further embodiment, an oligonucleotide of the invention can form a triple helix with a MIF1 DNA molecule. Generally, oligonucleotides are prepared synthetically, preferably on a nucleic acid synthesizer. Accordingly, oligonucleotides can be prepared with non-naturally occurring phospohoester analog bonds, such as thioester, bonds, etc.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in in a cell when RNA polymerase transcribes the coding sequence into mRNA, which is then trans-RNA spliced (if the coding sequence contains introns) and translated into the protein encoded by the coding sequence.

As used herein, the term "homologous" in all its grammatical forms and spelling variations refers to the relationship between proteins that possess a "common evolutionary origin," including proteins from superfamilies (e.g. the immunoglobulin superfamily) and homologous proteins from different species (e.g., myosin light chain, etc.) (Reeck et al. 1987, Cell 50:667). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A gene encoding MIF1, whether genomic DNA or cDNA, can be isolated from any source, particularly from a human cDNA or genomic library. Methods for obtaining MIF1 gene are well known in the art, as described above (see, e.g., Sambrook et al., 1989, supra).

Accordingly, any animal cell potentially can serve as the nucleic acid source for the molecular cloning of a MIF1 gene. The DNA may be obtained by standard procedures known in the art from cloned DNA (e.g., a DNA "library") and preferably is obtained from a cDNA library prepared from tissues with high level expression of the protein (e.g., heart, pancreas and placenta cDNA, since these are the cells that evidence highest levels of expression of MIF1), by chemical synthesis, by cDNA cloning, or by the cloning of genomic DNA, or fragments thereof, purified from the desired cell (See, for example, Sambrook et al., 1989, supra; Glover, D M. (ed.), 1985, DNA Cloning: A Practical Approach, MRL Press, Ltd., Oxford, U K. Vol. I, II). Clones derived from genomic DNA may contain regulatory and intron DNA regions in addition to coding regions; clones derived from cDNA will not contain intron sequences. In a specific embodiment, MIF1 was isolated from a Hela cell library. Whatever the source, the gene should be molecularly cloned into a suitable vector for propagation of the gene.

Once the DNA fragments are generated, identification of the specific DNA fragment containing the desired MIF1 gene may be accomplished in a number of ways. For example, DNA fragments may be screened by nucleic acid hybridization to a labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. As noted above, the greater the degree of homology, the more stringent hybridization conditions can be used. In a specific embodiment, Northern hybridization conditions are used to identify mRNA splicing variants of an MIF1 gene.

Further selection can be carried out on the basis of the properties of the gene, e.g., if the gene encodes a protein product having the isoelectric, electrophoretic, amino acid composition, or partial amino acid sequence of MIF1 protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for MIF1. In a specific embodiment, the expressed protein is recognized by a polyclonal antibody that is generated against amino acids 16–28 of MIF1.

The present invention also relates to genes (e.g., cDNAs) encoding allelic variants, splicing variants, analogs, and derivatives of MIF1 of the invention, that have the same or homologous functional activity as MIF1, and homologs thereof from other species. The production and use of derivatives and analogs related to MIF1 are within the scope of the present invention. In a specific embodiment, the derivative or analog is functionally active, i.e., capable of exhibiting one or more functional activities associated with a full-length, wild-type MIF1 of the invention. In particular, such an analog or derivative can regulate MEKK activity. Alternatively, an allelic variant can comprise a mutation that results in the inability of MIF1 to regulate MEKK activity.

MIF1 derivatives can be made by altering encoding nucleic acid sequences by substitutions, additions or deletions that provide for functionally equivalent molecules. Preferably, derivatives are made that have enhanced or increased functional activity relative to native MIF1.

Due to the degeneracy of nucleotide coding sequences, other DNA sequences which encode substantially the same amino acid sequence as a MIF1 gene, including an amino acid sequence that contains a single amino acid variant, may be used in the practice of the present invention. These include but are not limited to allelic genes, homologous genes from other species, and nucleotide sequences comprising all or portions of MIF1 genes which are altered by the substitution of different codons that encode the same amino acid residue within the sequence, thus producing a silent change. Likewise, the MIF1 derivatives of the invention include, but are not limited to, those containing, as a primary amino acid sequence, all or part of the amino acid sequence of a MIF1 protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids, include aspartic acid and glutamic acid. Such alterations will not be expected to affect apparent molecular weight as determined by polyacrylamide gel electrophoresis, or isoelectric point:

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gin for Asn such that a free $CONH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces b-turns in the protein's structure.

The genes encoding MIF1 derivatives and analogs of the invention can be produced by various methods known in the art. The manipulations which result in their production can occur at the gene or protein level. For example, the cloned MIF1 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of MIF1, care should be taken to ensure that the modified gene remains within the same translational reading frame as the MIF1 gene, uninterrupted by translational stop signals, in the gene region where the desired activity is encoded.

Additionally, the MIF1-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated MIF1 gene, product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al. 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in PCR *Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enigmatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2 m plasmid.

Expression of MIF1 Polypeptides

The nucleotide sequence coding for MIF1, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding MIF1 of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding MIF1 and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant MIF1 protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding MIF1 is cultured in an appropriate cell culture medium under conditions that provide for expression of MIF1 by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of MIF1 protein may be controlled by any promoter/enhancer element known in the art, but these regulatory elements must be functional in the host selected for expression. Promoters which may be used to control MIF1 gene expression include, but are not limited to, the SV40 early promoter region (Benoist and Chambon, 1981. Nature 290:304–310), the promoter contained in the 3' long terminal repeat of Rous sarcoma virus (Yamamoto, et al., 1980, Cell 22:787–797), the herpes thymidine kinase promoter (Wagner et al. 1981, Proc. Natl. Acad. Sci. U.S.A. 78:1441–1445), the regulatory sequences of the metallothionein gene (Brinster et al., 1982, Nature 296:39–42); prokaryotic expression vectors such as the b-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase 1 gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515): insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985 Nature 318:533–538; Alexander et al., 1987. Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha-1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding a MIF1 of the invention can be identified by five general approaches: (a) PCR amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., b-galactosidase activity, thymidine kinase activity, resistance to antibiotics, transformation phenotype, occlusion body formation in baculovirus, etc.) caused by the insertion of foreign genes in the vector. In another example, if the nucleic acid encoding MIF1 is inserted within the "selection marker" gene sequence of the vector, recombinants containing the MIF1 insert can be identified by the absence of the MIF1 gene function. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al. 1988, Gene 67:31–40), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2 m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL 1393 (BamH1, SmaI, XbaI, EcoRI, NotI, XmaIII, BglII, and PstI cloning site; Invitrogen), pVL1392 (BglII, PstI, NotI XmaIII, EcoRI XbaI SmaI, and BamH1 cloning site; Summers and Invitrogen), and pBlueBacIII (BamHI, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and Bc/I cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive Rous Sarcoma Virus Long Terminal Repeat (RSV-LTR) promoter, hygromycin selectable marker; Invitrogen), pCEP4 (BamH1, SfiI, XhoI, NotI, NheI, HindIII, NheI, PvuII, and KpnI cloning site, constitutive human cytomegalovirus (hCMV) immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1 I, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamH1 cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and b-gal selection), pMJ601 (SalI, SmaI, AflI, NarI, BspMII, BamH1, ApaI, NheI, SacII, KpnI, and HindIII cloning site; TK- and b-gal selection), and pTKgptF1S (EcoRI, PstI, SalI, AccI, HindII, ShaI, BamH1, and Hpa cloning site, TK or XPRT selection).

Yeast expression systems can also be used according to the invention to express MIF1. For example, the non-fusion pYES2 vector (XbaI, SphI, ShoI, NotI, GstXI, EcoRI, BstXI, BamH1, SacI, KpnI, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification of proteins. Appropriate cell lines or host systems can be chosen to ensure the desired modification and processing of the foreign protein expressed. Expression in yeast can produce a biologically active product. Expression in eukaryotic cells can increase the likelihood of "native" folding. Moreover, expression in mammalian cells can provide a tool for reconstituting, or constituting, MIF1 activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624: Hartmut et al., Canadian Patent Application No. 2,012,311, filed Mar. 15, 1990).

Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Antibodies to MIF1

According to the invention, an MIF1 polypeptide produced recombinantly or by chemical synthesis, and fragments or other derivatives or analogs thereof, including fusion proteins, may be used as an antigen or immunogen to generate antibodies that recognize the MIF1 polypeptide. A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids.

An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Such antibodies include but are not limited to polyclonal, monoclonal, chimeric, single chain, Fab fragments, and an Fab expression library. The anti-MIF1 antibodies of the invention may be cross reactive, e.g., they may recognize MIF1 from different species. Polyclonal antibodies have greater likelihood of cross reactivity. Alternatively, an antibody of the invention may be specific for a single form of MIF1, such as murine MIF1. Preferably, such an antibody is specific for human MIF1.

Various procedures known in the art may be used for the production of polyclonal antibodies to MIF1 polypeptide or derivative or analog thereof. For the production of antibody, various host animals can be immunized by injection with the MIF1 polypeptide, or a derivative (e.g., fragment or fusion protein) thereof, including but not limited to rabbits, mice, rats, sheep, goats, etc. In one embodiment, the MIF1 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guenin*) and *Corynebacterium parvum*.

For preparation of monoclonal antibodies directed toward the MIF1 polypeptide, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals [International Patent Publication No. WO 89/12690, published 28 Dec. 1989]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for an MIF1 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain Fv (scFv) antibodies [U.S. Pat. Nos. 5,476,786 and 5,132,405 to Huston; U.S. Pat. No.

4,946,778] can be adapted to produce MIF1 polypeptide-specific single chain antibodies. An additional embodiment of the invention utilizes the techniques described for the construction of Fab expression libraries [Huse et al., Science 246:1275–1281 (1989)] to allow rapid and easy identification of monoclonal Fab fragments with the desired specificity for an MIF1 polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example) western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an MIF1 polypeptide, one may assay generated hybridomas for a product which binds to an MIF1 polypeptide fragment containing such epitope. For selection of an antibody specific to an MIF1 polypeptide from a particular species of animal, one can select on the basis of positive binding with MIF1 polypeptide expressed by or isolated from cells of that species of animal.

The foregoing antibodies can be used in methods known in the art relating to the localization and activity of the MIF1 polypeptide, e.g., for Western blotting, imaging MIF1 polypeptide in situ, measuring levels thereof in appropriate physiological samples, etc. using any of the detection techniques mentioned above or known in the art.

In a specific embodiment, antibodies that agonize or antagonize the activity of MIF1 polypeptide can be generated. Such antibodies can be tested using the assays described infra for identifying ligands. In particular, such antibodies can be scFv antibodies expressed intracellularly.

Screening Assays

Identification and isolation of a gene encoding an MIF1 of the invention provides for expression of MIF1 in quantities greater than can be isolated from natural sources, or in indicator cells that are specially engineered to indicate the activity of MIF1 expressed after transfection or transformation of the cells. Accordingly, in addition to rational design of agonists and antagonists based on the structure of MIF1 polypeptide, the present invention contemplates an alternative method for identifying specific ligands of MIF1 using various screening assays known in the art.

Any screening technique known in the an can be used to screen for MIF1 agonists or antagonists or to screen for antagonists of MIF1/MEKK1 binding.

The present invention contemplates screens for small molecule ligands or ligand analogs and mimics, as well as screens for natural ligands that bind to and agonize or antagonize activates MIF1 in vivo. For example, natural products libraries can be screened using assays of the invention for molecules that agonize or antagonize MIF1 activity.

Molecules or compounds that agonize or antagonize MIF1 activity and/or that modulate MIF1/MEKK interaction may provide new venue for preventing and/or treating pathologies which involve, a deregulation of cellular apoptosis or other pathologies as inflammation and asthma, immunosuppression, cardiac ischemia or hypertrophy, myelodysplasic syndromes, neurodegenerative disorders, hepatic degenerative disorders, autoimmune diseases, viral infections, AIDS, pathologies related with angiogenesis disorders, rhumathoid arthritis, defect of wound healing, atherosclerosis, diabetic retinopathy, Kaposi sarcoma, psoriasis etc.

With this regards, the invention also provides for a method for treating an individual having need to inhibit or activate MIF1 activity or having need to regulate MEKK activity comprising administering a therapeutically effective amount of molecules or compounds that agonize or antagonize MIF1 activity and/or that modulate MIF1/MEKK interaction. The invention provides for the use of such molecules or compound for the preparation of a medicament.

Knowledge of the primary sequence of MIF1, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, Science 249:386–390 (1990); Cwirla, et al., Proc. Natl. Acad. Sci., 87:6378–6382 (1990); Devlin et al., Science, 249:404–406 (1990)], very large libraries can be constructed ($10^6$–$10^8$ chemical entities). A second approach uses primarily chemical methods, of which the Geysen method [Geysen et al., Molecular Immunology 23:709–715 (1986); Geysen et al. J. Immunologic Method 102:259–274 (1987)] and the method of Fodor et al. [Science 251:767–773 (1991)] are examples. Furka et al. [14th International Congress of Biochemistry, Volume 5, Abstract FR:013 (1988); Furka, Int. J. Peptide Protein Res. 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:10700–4 (1993); Ohlmeyer et al., Proc. Natl. Acad. Sci. USA 90:10922–10926 (1993); Lam et al., International Patent Publication No. WO 92/00252; Kocis et al., International Patent Publication No. WO 9428028, each of which is incorporated herein by reference in its entirety], and the like can be used to screen for MIF1 ligands according to the present invention.

The screening can be performed with recombinant cells that express the MIF1, or alternatively, using purified protein, e.g., produced recombinantly, as described above.

For example, the ability of labeled, soluble MIF1 that includes the MEKK-binding portion of the molecule, can be used to screen libraries, as described in the foregoing references.

In one embodiment, MIF1 may be directly labeled. In another embodiment, a labeled secondary reagent may be used to detect binding of an MIF1 to a molecule of interest, e.g., a molecule attached to a solid phase support. Binding may be detected by in situ formation of a chromophore by an enzyme label. Suitable enzymes include, but are not limited to, alkaline phosphatase and horseradish peroxidase. In a further embodiment, a two color assay, using two chromogenic substrates with two enzyme labels on different acceptor molecules of interest, may be used. Cross-reactive and singly-reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Two color assays may be performed with two or more colored latex beads, or fluorophores that emit at different wavelengths. Labeled may be detected visually or by mechanical/optical means. Mechanical/optical means include fluorescence activated sorting, i.e. analogous to FACS, and micromanipulator removal means.

As exemplified herein, the level of the MIF1 protein can be evaluated by metabolic labeling of the proteins. As the metabolic labeling occurs during in vitro incubation of the tissue biopsy in the presence of culture medium supplemented with $[^{35}S]$-methionine, the level of each of the markers detected may be affected by the in vitro conditions. In addition to metabolic (or biosynthetic) labeling with $[^{35}S]$-methionine, the invention further contemplates labeling with $[^{14}C]$-amino acids and $[^3H]$-amino acids (with the tritium substituted at non-labile positions). Thus, a sample or library of compounds can be directly analyzed after labeling of the proteins therein, e.g., by calorimetric staining using silver, gold, coomassie blue, or amido-schwartz, to mention a few techniques; isotopic labeling, e.g., with $[^{32}P]$-orthophosphate, $[^{125}I]$, $[^{131}I]$; fluorescent or chemiluminescent tags; and immunological detection with labeled antibody or specific binding partner of a marker.

MIF1 cDNA and derivatives can also be used in a two-hybrid system in yeast screening to identify ligands to MIF1, agonists or antagonists of MIF1/MEKK1 binding and to identify MAP4K that are able to phosphorylate MEKK1.

Gene Therapy and Transgenic Vectors

As discussed above, a "vector" is any means for the transfer of a nucleic acid according to the invention into a host cell. Preferred vectors are viral vectors, such as retroviruses, herpes viruses, adenoviruses, and adeno-associated viruses. Thus, a gene encoding an anti-angiogenic protein or polypeptide domain fragment thereof is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Expression vectors of the invention can be used, as pointed out above, both to transfect cells for screening or biological testing of modulators of MIF1 activity, or for delivery of a MIF1 gene or MIF1 antisense gene in vivo or ex vivo for gene therapy, e.g., to increase or decrease the level of MIF1 activity. A vector that expresses an anti-MIF1 scFv can also be introduced using the techniques discussed below.

Viral vectors commonly used for in vivo or ex vivo targeting and therapy procedures are DNA-based vectors and retroviral vectors. Methods for constructing and using viral vectors are known in the art [see, e.g., Miller and Rosman, *BioTechniques* 7:980–990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Defective viruses, which entirely or almost entirely lack viral genes, are preferred. Defective virus is not replication competent after introduction into a cell, and thus does not lead to a productive viral infection. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., *Molec. Cell. Neurosci.* 2:320–330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [*J. Clin. Invest.* 90:626–630 (1992); see also La Salle et al., *Science* 259:988–990 (1993)]; and a defective adeno-associated virus vector [Samulski et al., *J. Virol.* 61:3096–3101 (1987); Samulski et al., *J. Virol.* 63:3822–3828(1989); Lebowski et al., *Mol. Cell. Biol.* 8:3988–3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

Naturally, the invention contemplates delivery of a vector that will express a therapeutically effective amount of MIF1 for gene therapy applications. The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Any vector, viral or non-viral, of the invention will preferably be introduced in vivo in a pharmaceutically acceptable vehicle or carrier. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E W. Martin.

Adenovirus Vectors

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1–L5.

In a preferred embodiment the adenoviral vector has a deletion in the E1 region (Ad 1.0). Examples of E1-deleted adenoviruses are disclosed in EP 185,573 the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-Associated Virus Vectors

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterised. It encompasses approximately 4700 bases and contains an inverted terminal repeat (ITR) region of approximately 145 bases at each end, which serves as an origin of replication for the virus. The remainder of the genome is divided into two essential regions which carry the encapsulation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088 WO93/09239;U.S. Pat. No. 4,797,368,U.S. Pat. No. 5,139,941 EP488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsulation genes (rep and cap genes), into a cell line which is infected with a human helper virus (for example an adenovirus). The AAV recombinants which are produced are then purified by standard techniques.

The invention also relates, therefore, to an AAV-derived recombinant virus whose genome encompasses a sequence encoding a nucleic acid encoding an anti-angiogenic factor flanked by the AAV ITRs. The invention also relates to a plasmid encompassing a sequence encoding a nucleic acid encoding A an anti-angiogenic factor flanked by two ITRs from an AAV. Such a plasmid can be used as it is for transferring the nucleic acid sequence, with the plasmid, where appropriate, being incorporated into a liposomal vector (pseudo-virus).

Retrovirus Vectors

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764: Temin et al., U.S. Pat. No. 4,980,289; Markowitz et al., 1988, J. Virol. 62:1120; Temin et al., U.S. Pat. No. 5,124,263; EP 453242, EP 178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et al., 1993, Blood 82:845. The retroviruses are integrating viruses which infect dividing cells. The retrovirus genome includes two LTRs, an encapsulation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsulation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsulation sequences which may include a part of the gag gene (Bender et al., J. Virol. 61 (1987) 1639) Recombinant retroviral vectors are purified by standard techniques known to those having ordinary skill in the art.

Retroviral vectors can be constructed to function as infections particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal but retain the structural genes required to package the co-introduced virus engineered to contain the heterologous gene and the packaging signals. Thus, the viral particles that are produced are not capable of producing additional virus.

Targeted gene delivery is described in International Patent Publication WO 95/28494, published October 1995.

Non-Viral Vectors

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., Proc. Natl. Acad. Sci. U.S.A. 84:7413–7417 (1987); see Mackey, et al., Proc. Natl. Acad. Sci. U.S.A. 85:8027–8031 (1988); Ulmer et al., Science 259:1745–1748 (1993)]. The use of cationic lipids may promote encapsulation of negatively charged nucleic acids, and also promote fusion with negatively charged cell membranes [Felgner and Ringold, Science 337:387–388 (1989)]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267:963–9.67(1992); Wu and Wu J. Biol. Chem. 263:14621–14624(1988); Hartmut et al., Canadian Patent Application No. 2,012,311, filed Mar. 15, 1990; Williams et al., Proc. Natl. Acad. Sci. USA 88:2726–2730 (1991)]. Receptor-mediated DNA delivery approaches can also be sued [Curiel et al., Hum. Gene Ther. 3:147–154 (1992); Wu and Wu J. Biol. Chem. 262:4429–4432 (1987)].

The present invention may be better understood by reference to the following non-limiting Examples, which are provided as exemplary of the invention.

EXAMPLES

Material and Methods

Yeast strain. The strain YCM17 of the genus S. cerevisiae (MATa, ura3-52, his3-200, ade2-101, lys2-801, trp1-901 leu2-3,112, can1, gal4-542, gal80-538, met16:: URA3-pGAL1/10-LacZ.) was used as a tool for screening the Hela cell fusion bank via the two-hybrid system.
It was cultivated on the following culture media:
YPD complete medium:—Yeast extract (10 g/l) (Difco)
    Bacto-peptone (20 g/l) (Difco)
    Glucose (20 g/l) (Merck)
This medium was rendered solid via the addition of 20 g/l of agar (Difco).
YNB minimal medium:—Yeast Nitrogen Base (with no amino acids) (6.7 g/l) (Difco)

Glucose (20 g/l) (Merck)

This medium can be rendered solid by the addition of 20 g/l of agar (Difco).

To permit the growth of auxotrophic yeasts on this medium, it is necessary to add to it amino acids or nitrogen bases on which they are dependent at 50 mg/l.

Bacterial strain. The strain TG1 of *Escherichia coli* of the genotype supE, hsdD5, thi, D(lac-proAB), F'[tra D36 proA$^+$ B$^+$lacI$^q$lacZDM15] was used as a means to amplify and isolate the recombinant plasmids utilized.

It was cultivated on:

LB medium:—NaCl (5 g/l) (Difco)
Bacto-tryptone (10 g/l) (Difco)
Yeast extract (5 g/l) (Difco)

This Medium was rendered solid by the addition de 20 g/l of agar (Difco). Ampicillin (100 µg/ml) permits selection of the bacteria that have received the plasmids that carry the gene imparting resistance to this antibiotic as a marker.

Plasmids. Vectors of the pGBT series (Clontech or described by Roder K H, Wolf S S, and Schweizer M (1996) Anal. Biochem 241:260–2) were employed. These are shuttle plasmids that possess an origin of bacterial and yeast replication permitting them to replicate with a high copy number in these two microorganisms. These plasmids contain a multiple cloning site located downstream from the coding sequence for the DNA binding domain of GAL4 and upstream from a terminator codon in order to form a fusion protein. They also contain the gene TRP1 of *S. cerevisiae*, which permits the yeasts of the genotype trp1 to be complemented in order to select them on a minimal medium that does not contain any tryptophan. This vector carries the gene imparting resistance to ampicillin that permits selection of the bacteria that possess it on a medium containing ampicillin.

Vectors of the PGAD series (Clontech) were also employed. These are vectors that permit the expression in the yeast of fusion proteins between the transactivator domain of GAL4 and a protein that is of interest or is coded by cDNA coming from a Hela cell bank, inserted at the level of the EcoRI XhoI sites.

Vectors pAV3 and pTD1 (Clontech), were used as positive control vectors to indicate a protein—protein interaction between the protein p53 and the T antigen.

Bluescript series vectors (Stratagene), were used. These vectors permit cloning to be performed just like the pMTL series (Chambers et al.; Gene 1988, 68, pp 139–149).

In addition, the vector pcDNA3 (Invitrogen) and derivative vectors (pSG42 and pCNW8), which permit the expression of proteins in mammal cells under the control of the CMV promoter, were used.

Also, the vector pCRII (Invitrogen), which permits cloning of PCR fragments, was used.

The genetic engineering techniques used to clone and insert cDNAs into these plasmids employed routine protocols (Maniatis T. et al., "Molecular Cloning, a Laboratory Manual," Cold Spring Harbor Laboratory, Cold Spring Harbor, N.Y., 1982; Ausubel F. M. et al. (eds.), "Current Protocols in Molecular Biology," John Wiley & Sons, New York, 1987).

Preparation of the plasmid DNA. Large quantities of DNA were prepared using Promega's rapid DNA preparation kit in accordance with the manufacturer's instructions. Small quantities of DNA were prepared in the following manner: bacteria containing the plasmid were cultivated for at least 4 hours in 2 ml of LB medium in a shaker with agitation. They were then centrifuged for 2 minutes at 14,000 rpm in Eppendorf tubes, then the concentrate was put back in suspension in 100 µl of solution I (50 mM of glucose, 25 mM of Tris-HCl pH 8 buffer, 10 mM of EDTA pH 8), lysed with 200 µl of solution II (0.2 M of NaOH, 1% SDS). The lysis solution was then neutralized with 150 µl of solution III (3 M of potassium acetate, 11.5% (v/v) glacial acetic acid). After agitation of the tubes until a flocculent precipitate was obtained, 150 µl of a mixture of phenol/chloroform (50% phenol and 50% chloroform saturated in water) was added, and the entire mixture was agitated for 30 seconds. The aqueous phase containing the DNA was recovered after centrifugation for 2 minutes at 14,000 rpm. The DNA was then precipitated via the addition of 0.5 volume of isopropanol, then centrifuged for 5 minutes at 14,000 rpm and air-dried in order to finally be dissolved in 20 µl of TE-RNAse (solution of 10 mM of Tris-HCl and 1 mM of EDTA with 50 µg/ml of RNAse).

Enzyme amplification of DNA by Polymerase Chain Reaction (PCR). PCR reactions were carried out in a final volume of 100 µl in the presence of the double stranded DNA, dNTP (0.2 mM), PCR buffer (10 mM of Tris-HCL pH 8.5, 1 mM of MgCl$_2$, 5 mM of KCl, gelatin 0.01%), 0.5 µg of each of the oligonucleotides, and 2.5 IU of Ampli Taq DNA polymerase (Perkin Elmer) with or without formamide (5%). The mixture was covered with 2 drops of paraffin oil to limit evaporation of the sample. The equipment used was Appligene's "Crocodile II." Denaturation was effected at a temperature of 90° C. for denaturation of the helix, a temperature for hybridization of the oligonucleotides to the denatured (single-stranded) DNA that was 5 to 10 degrees lower than the temperature for the separation of the oligonucleotides, and a temperature of 72° C. for elongation by the enzyme. The fragments obtained by PCR, which were used for cloning, were systematically resequenced once they were cloned, so as to verify the absence of any mutations that might have occurred during the amplification.

The oligodeoxynucleotides were chemically synthesized according to the phosphoramidite method by utilizing β-cyanoethyl protector groups (Sinha, 1984). After synthesis, the protector groups were eliminated by treatment with ammonia, and two precipitations with butanol permitted purification and concentration of the oligodeoxynucleotides (Sawadogo, 1991). The DNA concentration was determined by measuring the optical density at 260 nm.

Ligations. All of the ligation reactions were carried out at +14° C. for one night in a final volume of 10 µl in the presence of 100 to 200 ng of vector, 0.5 to 2 µg of insert, 40 IU of enzyme T4 DNA ligase (Biolabs), and a ligation buffer (50 mM of Tris-HCl pH 7.8; 10 mM of MgCl$_2$; 10 mM of DTT; 1 mM of ATP). The negative control was formed by the ligation of the vector in the absence of the insert.

The filling of the prominent 5' ends was carried out, as needed, before ligation via the Klenow fragment of DNA Polymerase I of *E. coli*(Biolabs) according to the supplier's specifications. The destruction of the prominent 3' ends was accomplished in the presence of DNA Polymerase of the T4 phage (Biolabs) used according to the manufacturer's recommendations.

Transformation of the bacteria. The entire ligation volume (10 µl) was used to transform the TGI bacteria, which were rendered competent by the method of Chung et al. (1988, Proc. Natl. Acad. Sci. 86:2172–2175). The TGI bacteria were placed in culture in a liquid LB medium for several hours in an incubator with agitation at 37° C. until an OD of 0.6 was obtained at 600 nm. The medium was then centrifuged at 6,000 rpm for 10 nm. The bacteria were rendered competent by dissolving the bacterial concentrate in a volume of TSB (LB medium+100 g/l of PEG 4000, 5% DMSO, 10 mM of $MgCl_2$, 10 mM of $MgSO_4$) corresponding to 1/10 of the volume of the medium of the initial culture. After incubation at 4° C. for 30 to 60 minutes, 200 µl of bacteria were placed in contact with the ligation products for 15 minutes on ice. After the addition of 200 µl of LB [medium], the bacteria were incubated for 30 mn at 37° C., then spread out on an LB+ampicillin medium.

Separation and extraction off the DNA. The separation of the DNA was performed by electrophoresis as a function of their size. In order to do this, different gels were used depending on the size of the fragments to be separated:

1% agarose gel (Gibco BRL) in a TBE buffer (90 mM of Tris base; 90 mM of borate 2 mM of EDTA) to separate large DNA fragments (greater than 500 bp);

2% NuSieve agarose gel (FMC Bioproducts) in a TBE buffer to separate small fragments (less than 500 bp).

Migration on agarose gel or on polyacrylamide gel was carried out in a TBE buffer and in the presence of a molecular weight marker (1 Kb ladder, Gibco BRL). The DNA was mixed with 1/10 of the deposit volume of blue (200 g/l of Ficoll. 0.5 g/l of bromophenol blue, 50 mM of EDTA) before being deposited on the gel. After migration at 100 Volts and staining with ethidium bromide (concentration 0.5 µg/ml of gel), the bands were viewed under a UV lamp.

Extraction of the DNA from the band of an agarose gel was carried out by means of electroelution as follows: The piece of gel containing the DNA fragment was cut out with a scalpel and placed in a dialysis tube closed with two clamps and containing 100 to 500 µl of TBE. The entire mixture was placed in an electrophoresis tank, where it was subjected to an electrical field of 100 Volts. After being removed from the gel, the DNA was then purified by means of two extractions with phenol/chloroform followed by two extractions with chloroform, then precipitated in the presence of 0.3 M of sodium acetate and 2.5 volume of absolute alcohol. After centrifugation (5 mn at 14,000 rpm), the DNA concentrate was dried and then dissolved in 20 µl of water.

Fluorescent sequencing of plasmid DNA. The sequencing was carried out according to Sanger's method using 4 dideoxyribonucleotides possessing a different fluorescent marker. The incorporation of one of these dideoxyribonucleotides caused a halt in the replication by the polymerase Taq of the DNA to be sequenced. This reaction yielded DNA fragments of various sizes, all of which were terminated at 3' by one of the 4 dideoxyribonucleotides. One µg of a plasmid and 4 picomoles of a primer were added to 9.5 µl of a "premix" supplied by Applied Biosystems under the trademark PRISM©. The final volume had to be 20 µl in order to perform a PCR for 25 cycles, broken down into a denaturation phase at 96° C. for 30 seconds, a hybridization phase at 50° C. for 15 seconds, and an elongation phase at 60° C. for 4 minutes. DNA fragments obtained after amplification were purified on an exclusion column (Chromaspin-30 from Clontech) and were then dried in the Speed Vac. All of the dried material was dissolved in 5 µl of a mixture made up of 24 µl of EDTA (50 mM) and 120 µl of deionized formamide. After denaturation at 96° C. for 3 minutes, 3 to 5 µl were deposited on an electrophoresis gel. The different DNA fragments were separated according to their size and then successively passed in front of a laser reader of the ABI 370 DNA sequencer (Applied Biosystems), where the different fluorescent chromophores were detected.

Preparation of plasmids from the Hela cell bank (Clontech®). The Hela cell cDNA bank was obtained in the form of bacteria. After verification of the titer of the bank, 2 µl of bacteria from the Hela cell fusion bank, which had been previously placed in 8 ml of LB [medium], were spread out in a non-convergent manner over a solid medium in order to maintain the representative nature of this bank. We thus spread [the bacteria on] 16 770 $cm^2$ dishes containing an LB+ampicillin medium. For each of the dishes, the colonies that appeared were dissolved in 30 ml of liquid LB+ampicillin [medium]. The suspensions obtained were then placed in an Erlenmeyer [flask] and incubated in a shaker at 37° C. for 3 hours. The DNA was then extracted from these strains by means of the Maxiprep technique. The concentration of DNA was determined at 260 nm.

Transformation of the yeast by a plasmid. Yeast cells cultivated in 100 ml of liquid medium were collected after centrifugation at 3,000 rpm for 3 minutes and placed in suspension in 1 ml of sterile water. After centrifugation at 3,000 rpm for 3 minutes, the cellular concentrate was placed back in suspension in 1 ml of sterile water, then centrifuged again. This operation was repeated once again in order to eliminate any trace of the culture medium. The yeast cells were then dissolved in 1 ml of transformation solution I (0.1 M of LiAc, 10 mM of Tris-HCl pH 7.5, 1 mM of EDTA), and centrifuged at 3,000 rpm for 3 minutes. The cellular concentrate was again dissolved in 1 ml of transformation solution I. Fifty µl of this suspension were mixed with 50 µg of DNA of salmon sperm and 1 to 5 µg of plasmid DNA. Three hundred µl of a transformation solution II (0.1 M of LiAc, 10 mM of Tris-HCl pH 7.5, 1 mM of EDTA in 40% $PEG_{4000}$) were added next, then the entire mixture was incubated at 28° C. for 30 minutes. Thermal shock was then applied to the transformation mixture in a water bath at 40° C. for 15 minutes, then the entire mixture was centrifuged at 15,000 rpm for 1 min in order to collect the cellular concentrate. This sib concentrate was dissolved in 200 µl of water, then spread over an agar minimal medium that did not contain any amino acids corresponding to the markers supplied by the transforming plasmid. The yeasts were then cultivated for 72 hours at 28° C.

Transformation of the yeast by the Hela cell cDNA bank involved a different procedure. The yeast employed contained the plasmid pCM433, which permitted the expression of MEKK fused to the DNA binding domain of GAL4. It was cultivated in 250 ml of YPG minimal medium at 28° C. under agitation to a density of $10^7$ cells/ml. The cells were collected by means of centrifugation at 3,000 rpm for 10 minutes and were dissolved in 250 ml of water. After another centrifugation, the cellular concentrate was dissolved in 100 ml of water and centrifuged again. The concentrate was then dissolved in 10 ml of transformation solution I and incubated for 1 hour at 28° C. under agitation. After centrifugation, the cells were once again dissolved in 2.5 ml of transformation solution I, 100 µl of Hela cell cDNA bank, and 20 ml of transformation solution II, then incubated for 1 hour at 28° C. under agitation. Thermal shock was performed on this transformation mixture at 42° C. for 20 minutes. Centrifugation (3,000 rpm for 5 nm) was repeated 3 times consecutively, each time dissolving the concentrate in 10 ml of sterile water. The third time, the concentrate was dissolved in 2.5 ml of sterile water. Thus the PEG that was toxic for the cells was eliminated. 2.4 ml of this suspension were used to seed 250 ml of minimal medium containing the amino acids His, Lys, and Met and the bases Ura and Ade, and were cultivated for one night in a shaker at 28° C. The overnight culture was centrifuged (3,000 rpm for 5 nm) and washed with sterile water two times in a row. The concentrate was then dissolved in 2.5 ml of water. 2.4 ml, the volume of which was increased to 10 ml in sterile water, were used to seed 10 435-$cm^2$ dishes containing a YNB+Lys+Met+His+Ade medium, which were incubated for 3 days.

Preparation of the yeast genomic and plasmid DNA. An average yeast clone aliquot was placed in 200 μl of a TELT solution (2% Triton X100, 1% SDS, 100 mM of NaCl, 10 mM of Tris pH 8, 1 mM of EDTA), in the presence of 3 g of glass beads 450 μm in diameter and 200 μl of phenol/chloroform. This mixture was vortexed for 15 minutes, then centrifuged for 2 minutes at 14,000 rpm. The supernatant was collected without taking any of the protein cake, and the DNA contained in this phase was precipitated with 2.5 volumes of absolute alcohol. After centrifugation for 2 minutes at 14,000 rpm, the DNA concentrate was dried and dissolved in 20 μl of TE-RNAse. This DNA solution, which corresponds to a mixture of genome and plasmid DNA, was used directly to transform bacteria. Only the plasmid DNA was able to replicate in the bacteria and was able to be analyzed by means of the miniprep technique.

β-galactosidase activity test. A sheet of nitrocellulose had previously been placed over the Petri dish containing the individual yeast clones. Due to the phenomenon of adsorption, a true image of the placement of the clones was obtained. This sheet was then plunged into liquid nitrogen for 30 seconds in order to cause the yeasts to burst and, in this way, to release the β-galactosidase activity. After thawing, the sheet of nitrocellulose was deposited, colonies facing up, in another Petri dish containing Whatman paper that had previously been saturated with 1.5 ml of PBS solution (60 mM of $Na_2HPO4$, 40 mM of $NaH_2PO_4$, 10 mM of KCl, 1 mM of $MgSO_4$, pH 7) and 10 to 30 μl of X-Gal (5-bromo-4-chloro-3-indoyl-β-D-galactoside) with 50 mg/ml of N,N-dimethylformamide. The dish was then placed in an oven at 37° C. with the cover closed to prevent desiccation. The time for the blue stain to appear varied greatly, from a few minutes to several hours. This test was conducted in the presence of a positive control, the interaction of which was known and which turns blue rapidly.

Transfection of CHO-K1 cells. CHO-K1 cells were grown in complete medium (HAM's F12, 10% heat inactivated foetal bovine serum, 1% penicilline, 1% glutamine). Cells ($1.10^5$ cells/well) were seeded in 6-well plates and grown in complete medium during 24 h. Cells were then transfected with a total amount of 1 μg/well (pCDNA3 or pCM562) of plasmids using liposome formulation from GIBCO-BRL (Lipofectamine reagent) and according recommendations from the manufacturer. 4 days after transfection, cells were seeded in 10 cm Petri dishes and incubated with 500 μg/ml of G418 during 2 weeks. Resistant cells were then pooled and expanded with G418 until analysing and/or freezing.

Cellular extracts and protein expression analysis by PAGE-SDS: Cells were washed with PBS (1.06 mM KH2PO4, 154 mM NaCl, 5.6 mM Na2HPO4) and harvested in HNTG lysis buffer [Hepes pH 7.4 50 mM, NaCl 150 mM, Triton X100 1%, Glycerol 10%] buffer. After a 30 min lysis, cellular extracts were spinned (10 min, 2000 rpm, room temperature) and protein in supernatants were quantified using a colorimetric assay (Pierce). After heat denaturation, 10 μg of cellular extracts were separated on 10% Tris-glycine PAGE-SDS and electro-blotted onto PVDF membranes. Blots were saturated with 2% dried milk in TBS [Tris pH 7.5 mM 20 mM, NaCl 150 mM]-Tween 0.1% 16 h at 4° C. Myc-tagged-MIF1/MSP58 protein was detected using mouse anti-myc antibody and ECL revelation system (Amersham) using an anti-mouse antibody coupled to HRP enzyme as secondary antibody.

Generation of stable clones expressing Myc-tagged MIF1/MSP58 protein. Stable clones of expressing MIF1/MSP58 protein were obtained by cloning of individual cells. Cellular suspensions containing approximatively 0.1 cell/ 200 μl were distributed in 96-wells plates (200 μl/well) and incubated at 37° C. during several days (3 plates were prepared). After 4 weeks of growth, 36 clones were obtained and cellular extracts were analyzed by immunobloting using anti-myc antibody in order to detect the MIF1/MSP58 protein.

Analysis of JNK kinase activity in cells treated smith external stimuli. Cells ($2.10^5$/well) were seeded in 6-well plates and incubated in complete medium during 24 h. 200 μM of Sorbitol (freshly diluted in PBS) were then added and cells were incubated during 5, 15 or 30 min. Control cells were treated with 200 μl of PBS. After incubation, cells were washed rapidly with PBS and harvested in 200 μl of b-glycerophosphate buffer (80 mM b-glycerophosphate pH 7.4, 20 mM EGTA pH 8, 15 mM $MgCl_2$) supplemented with inhibitors of proteases PIC (0.1 mM Pefabloc, 10 μg/ml Aprotinine, 10 μg/ml Leupeptine, 1 μg/ml Antipain, 10 μg/ml Benzamidine, 1 g/ml Soybean Trypsin inhibitor, 1 μg/ml chymostatin, 1 μg/ml PepstatinA). Cells were then sonicated (6×30 sec) and cell extracts were cleared by ultra-centrifugation at 100,000 rpm during 30 minutes at 4° C. Supernatants (cytosolic extracts) were stored at −80° C. Protein concentrations were determined with Pierce reagent. 500 ng of cellular extracts were used for in vitro phosphorylation of GST-cJun (1/223) recombinant protein as substract (2.5 μg) in 20 mM HEPES pH 7.4, 5 mM $MgCl_2$, 2 mM DTT, 2 mM EGTA. Reaction mixture was supplemented with PKI (20 μg/ml), Na3VO4 (1 mM), ATP (25 μM) and $^{33}$PgATP 3 μCi. Samples were incubated 10 minutes at 30° C. and reaction was stopped by addition of Laemmli loading buffer (5×). Proteins were heat denaturated (95° C. 10 min) before being separated onto a 10% Tris-Glycine PAGE-SDS. Phosphorylated GST-Jun (1–223) protein was quantified using a phosphorimager (Packard).

Apoptosis assays. Cells ($2.10^5$/well) were seeded in 6-well plates and incubated in complete medium during 24 h. 200 mM of sorbitol was added and cells were incubated 24 h. Supernatant was then spinned (3500 rpm, 10 min, room temperature) to pellet apoptotic cells. Cells from plates were harvested by trypsination, washed with PBS and spinned. Pellet was then gently resuspended in cold ethanol and apoptosis was checked on 10000 cells by FACS analysis after propidium iodure staining (10 μg/ml) in presence of Rnase (1 mg/ml).

Construction of GST-MEKK1 plasmid. The HindIII [blunt]-XhoI fragment from pCM556 containing the whole MEKK1 (Russel, et al, 1995, J. Biol. Chem, vol 270 p11757) encoding sequence was cloned in pBCGST plasmid (Biotechniques, 1995, vol 18, p 142) cutted with Hpa1 and XhoI enzyme. The open reading frame of GST (N-Term) fused to MEKK1 sequence (C-Term) was verified by DNA sequencing. This plasmid was named pBCGST-MEKK1.

Analysis of MIF1/MSP58-MEKK1 interaction by GST pull-down. CHOMIF1/MSP58#34 ($6.10^5$ cells) were seeded into 10 cm Petri dishes and grown for 3 days in complete medium. Cells were then transfected with 10 μg of plasmid encoding for eithe GST-MEKK1 protein (pBCGST-MEKK1) or pBCGST as control using lipofectamine reagent (Gibco). Cells were then grown 24 h with complete medium. Cells were then incubated or not with 200 mM sorbitol during 30 minutes before lysis. Cells were washed with PBS and lysed at 4° C. in 500 μl of HNTG buffer containing proteases inhibitors PIC with 1 mM Na3VO4, 4 mM NaF, 10 μM AlCl3. Cells were then sonicated (6×30 sec) and cell extracts were cleared by centrifugation (10 min, 3000 rpm, 4° C.). Supernatants (500 μl) were incubated with 100 μl of HNTG-equilibrated GSH-Sepharose 4B (Pharmacia) 1 h at 4° C. with rotation. After centrifugation, GSH-sepharose was washed three times with 200 µl of HNTG. GST/GSH complexes were eluted with 100 µl of Tris HCl pH7.7, 50 mM, GSH 10 mM, 16 h at 4° C. GSH-sepharose was then spinned 30 min at 4000 rpm (4° C.) and an aliquot of 30 µl of eluate was loaded on 10% Tris-Glycine PAGE-SDS and analyzed by Western blot using anti-GST antibody (Tebu) and anti-myc antibody for MIF1/MSP58 detection.

Example 1

Construction of a Vector Permitting the Expression of a Fusion Protein between MEKK1 and the DNA Binding Domain of GAL4

The screening of a bank using the double-hybrid system requires that the protein MEKK1 be fused to the DNA binding domain of the transactivator protein GAL4. The expression of this fusion protein was effected by means of the vector pGBT9 (Materials and Methods, supra), into which was introduced, in the same reading frame as the sequence corresponding to the DNA binding domain of GAL4 (GAL4DB), a fragment EcoRI-XhoI from pCM411 (vector pMTL21 carrying the gene coding for MEKK1). The MEKK1 gene was inserted at the level of the EcoRI-SalI site of the plasmid pGBT9 in order to yield the plasmid pCM433.

The construct was sequenced, which permitted verification that the MEKK1 gene was, in fact, in the same open reading frame as that of the fragment corresponding to GAL4DB.

Example 2

Screening of the Hela Cell Fusion Bank

Screening of a fusion bank permits identification of the clones that produce the proteins fused to the transactivator domain of GAL4, which can interact with the protein that is of interest to us. This interaction permits reconstitution of a transactivator that will thus be able to induce the expression of the reporter genes URA3 and LacZ in the strain YCM17.

To perform this screening, a fusion bank created using human Hela cell cDNA was selected. Since this bank was supplied in the form of bacteria, the plasmid DNA of the bank was first purified.

Preparation of plasmid DNA from a fusion bank. The plasmid DNA from the Hela cell cDNA bank was extracted according to the Clontech® protocol (Materials and Methods). During this, preparation, it was important to preserve the representative nature of the bank, i.e., to preserve the number of independent plasmids that comprised it, which totaled 6×10$^6$ plasmids. In order to prevent loss of plasmids from the bank during this preparation, the plasmid DNA lot was obtained from a number of isolated bacteria colonies corresponding to a little over three times the representative nature of the bank, or 1.8×10$^7$ colonies.

Transformation by Hela cell bank and selection by the β-galactosidase activity test. During the screening, it was necessary to ensure a high probability that each independent plasmid from the fusion bank would be present in at least one yeast at the same time as the plasmid GAL4DB-MEKK1. This required good efficacy with respect to the transformation of the yeast. To this end, a yeast transformation protocol yielding an efficacy of 10$^5$ transformed cells per µg of DNA was chosen. In addition, since co-transformation of the yeast by two different plasmids reduces this efficacy, a yeast previously transformed by the plasmid pCM433 was used. This strain of yeast was transformed by 100 µg of plasmid DNA from the fusion bank. This quantity of DNA enabled us to obtain 1.5×10$^6$ transformed cells. The selection of transformed cells capable of reconstituting a functional GAL4 transactivator was performed on a YNB+Lys+Met+His+Ade medium. The lacZ activity of the clones obtained was verified.

By the end of this second selection, 46 clones with a phenotype Ura+ and bGal+ were obtained.

Example 3

Identification of Selected Plasmids Inserts

The plasmids extracted from the yeast were introduced in the bacteria, and were then prepared as described in Material and Methods. The sequencing was carried out using the complementary oligonucleotide CTATTCGATGATGAA-GATACCCC (SEQ ID NO:9) of the GAL4 TA region in the vicinity of the insertion site of the Hela cell cDNA bank, at 52 bp from the EcoRI site. Among the positive clones, several times the same cDNA representing an open reading frame (SEQ ID NO:1) but not presenting any significant homology with the sequences deposited in GenBank was found. This gene was called MIF1, and the corresponding plasmid from the cDNA bank was named pCM480. During this screening, four other sequences presented an open reading frame. Two were identical to sequences deposited in GenBank, namely, centrin (or caltractin) and UBC9, corresponding to the plasmids pCM479 and pCM481. One sequence presenting an open reading frame, from the plasmid pCM524, exhibited, on the protein level, a slight homology with a *Saccharomyces cerevisiae* gene. The last sequence presenting an open reading frame did not exhibit any homology with the sequences deposited in GenBank.

Example 4

Construction of a Vector Permitting the Expression in the Yeast of a Fusion Protein between Different Deletion Fragments of MEKK1 and the DNA Binding Domain of GAL4

Deletion of the Ncol—Ncol fragment of the plasmid pCM433 enabled plasmid pCM484 to be obtained. This vector permitted expression of amino acids 353 to 672 of MEKK1p in fusion with the DNA binding domain of Gal4p.

Deletion of the Pst1—Pst1 fragment of the plasmid pCM433 enabled plasmid pCM485 to be obtained. This vector permitted expression of amino acids 1 to 369 of MEKK1p in fusion with the DNA binding domain of Gal4p.

Deletion of the Sac1—Sac1 fragment of the plasmid pCM433 enabled plasmid pCM486 to be obtained. This vector permitted the expression of amino acids 287 to 672 of MEKK1p in fusion with the DNA binding domain of Gal4p.

Example 5

Localization of the Interaction Zone of the Proteins MEKK1 and MIF1

Yeast strain yCM17 was co-transformed by the different plasmids described in examples 1 and 4 and pCM480. β-gal activity was determined as described in Material and Methods, which permitted detection of the region of MEKK1 that is essential to its interaction with MIF1. In fact, the region from 287 to 353 seems to be important for interaction with MIF1 (see FIG. 1).

Example 6

Construction of a Vector Permitting Yeast Expression of a Fusion Protein between a Kinase-Dead Mutant of MEKK1 and of the DNA Binding Domain of GAL4

On plasmid pCM411, a PCR fragment was amplified with the oligonucleotides 9471 and 7841. This fragment was digested by Stu1 and PshA1, then ligated in the plasmid pCM433 cut by the restriction enzymes Stu1 et PshA1. The plasmid obtained was named pCM518.

Deletion of the Sac1—Sac1 fragment of plasmid pCM518 enabled plasmid pCM519 to be obtained. This vector permitted expression of amino acids 287 to 672 of kinase-dead MEKK1p in fusion with the DNA binding domain of Gal4p.

Deletion of the Nco1—Nco1 fragment of plasmid pCM518 enabled plasmid pCM520 to be obtained. This vector permitted expression of amino acids 353 to 672 of kinase-dead MEKK1p in fusion with the DNA binding domain of Gal4p.

Example 7

Construction of Vectors Permitting the Expression in the Yeast of a Fusion Protein between the Protein MEKK1 and the Transactivation Domain of GAL4 and between the Protein MIF1 and the DNA Binding Domain of GAL4

Expression of the fusion protein between the protein MEKK1 and the transactivation domain of Gal4 was achieved by means of the vector pGAD424 (Materials and Methods), in which was introduced, in the same reading frame as the sequence corresponding to the transactivation domain of Gal4 (GAL4TA), the fragment EcoR1-Xho1 from pCM411. The sequence of this plasmid was verified. This plasmid was named pCM490.

Expression of the fusion protein between the protein Mif1 and the DNA binding domain of Gal4 was achieved by means of the vector pGBT9+2 (Materials and Methods), in which was introduced, in the same reading frame as the sequence corresponding to the DNA binding domain of GAL4 (GAL4DB), the fragment EcoR1-Xho1 from pCM480. The sequence of this plasmid was verified. This plasmid was named pCM491.

Example 8

Localization of the Interaction Zone of the Proteins Mekk1p and Mifp1

The yeast strain yCM17 was transformed by the different plasmids described in examples 1, 4, 5, 6, and 7 at the same time as the plasmids pCM479, pCM480, pCM481, pCM482, and pCM524. The β-gal activity was detected as described in Material and Methods. The kinase activity of the protein MEKK1p seems to be important for its interaction with the protein MIF1p (pCM480), centrin (pCM479), and the proteins of the plasmids pCM482 and pCM524. In contrast, its interaction with the protein UBC9p (pCM481) does not seem to be affected by the absence of kinase activity (FIG. 1).

Example 9

Identification of the 5' Portion of the Gene Coding for the Protein MIF1p

From the collection of different ESTs of GenBank that present a high percentage of homology with the sequence of the insert of the plasmid pCM480 or between them (namely, EST no. W26888, access no, g1306116; EST no. AA134651, access no, g1695513; EST no. F12127, access no, g706460; EST no. W00383, access no. g1271822; EST no. T66207, access no, g675252; EST no. R28239, access no, g784374), a consensus sequence was able to be established. From this consensus, oligonucleotides were selected to amplify the 5' end of the sequence coding for the protein MIF1: 5'CGC GGA GAA ATT GTT GGA 3' (SEQ ID NO: 10) /5'CCG ATA TCG CAC TTG GTC CCC TTT GG 3' (SEQ ID NO: 11). After PCR had been carried out on the Hela cell cDNA bank, the fragment obtained was cloned in the plasmid pCR2 according to the instructions provided by the supplier in order to yield the plasmid pCM577. The sequence of the insert of the plasmid pCM577 was established, and it was determined that 603 out of 980 nucleotides of the fragment were identical to the 5' end of the insert of the plasmid pCM480. The other 377 nucleotides corresponded to a portion of the 5' end of the cDNA coding for the protein MIF1. Joining these two sequences permitted us to reconstitute the entire coding sequence of the protein MIF1 (SEQ ID NO:7).

Example 10

Construction of a Vector Permitting the Expression of the Protein MIF1 with a myc-Tag in Mammal Cells The oligonucleotides:
5' agcttccaccatggagcagaagct-gatctccgaggaggacctggaattctctcgag 3' (SEQ ID NO: 12) and
5'gatcctcgagagaattccaggtcctc-ctcggagatcagcttctgctccatggtgga 3' (SEQ ID NO:3) were paired and then ligated in the vector pcDNA3, which was digested by BamH1 and Hind3, to yield the plasmid pSG47. The Sma1-Apa1 fragment from vector pCM480 was inserted at the level of the EcoR5 and Apa1 sites of pSG47 to yield plasmid pCM500. Then the Apa1—Apa1 fragment was ligated at the level of the Apa1 site of pCM500 in the proper orientation to yield the plasmid pCM501. By PCR using oligonucleotides 5'CGG GAT CCA TGG ACA AAG ATT CTC AG 3' (SEQ ID NO:4) and 5' CCG ATA TCG CAC TTG GTC CCC TT GG 3' (SEQ ID NO: 11), the 5' end of the sequence coding for the protein Mif1p was amplified from the plasmid pCM577, which was digested by BamH1 and EcorV, and ligated in the vector pBluescriptII, which was also digested by BamH1 and EcorV. The plasmid obtained was named pCM525. The sequence of this plasmid was confirmed. The BamH1-PshA1 fragment of plasmid pCM525 was inserted at the level of the BamH1-PshA1 sites of plasmid pCM501. The resulting plasmid, pCM562, permitted the expression of the protein Mif1p with a myc-tag in mammalian cells under the control of the CMV promoter.

Example 11

Construction of a Vector Permitting the Expression of the Protein MEKK1p with an HA-Tag in Mammal Cells The oligonucleotides:
5'agcttccaccatgtatccgtatgatgtgcctgactacgcagaattctctcgag3' (SEQ ID NO: 5) and
5 gatcctcgagagaattctgcgtagtcaggcacatcatacggatacagggtgga 3' (SEQ ID NO: 6) were paired and then ligated in the vector pcDNA3, which was digested by BamH1 and Hind3, to yield the plasmid pSG52. The EcoR1-Xho1 fragment of plasmid pCM411 was inserted at the level of the EcoR1-Xho1 sites of plasmid pSG52. The resulting plasmid, pCM556, permitted the expression of MEKK1p with a tag HA in mammal cells under the control of the CMV promoter.

Example 12

Eukaryotic Expression of MIF1 in Vivo and in Vitro

Figure 2:
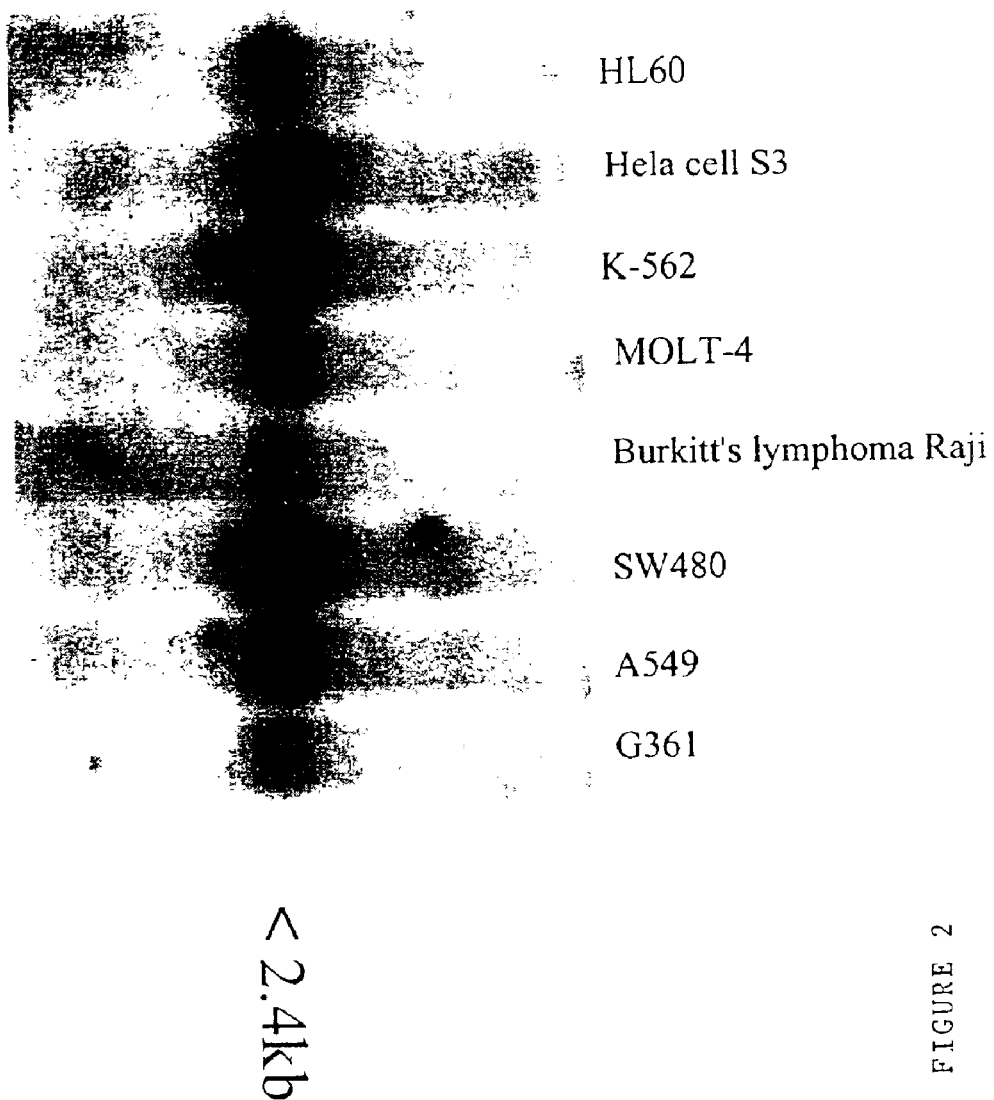
FIG. 2. Northern analysis of human tumor samples. The probe consists in a 1069 bp KpnI-BamHI fragment obtained from pCM562 plasmid (encoding full length MIF1). The probe was labeled with the standard procedure REDIPRIME (Amersham) and hybridized following the manufacturer instructions.
Figure 3:
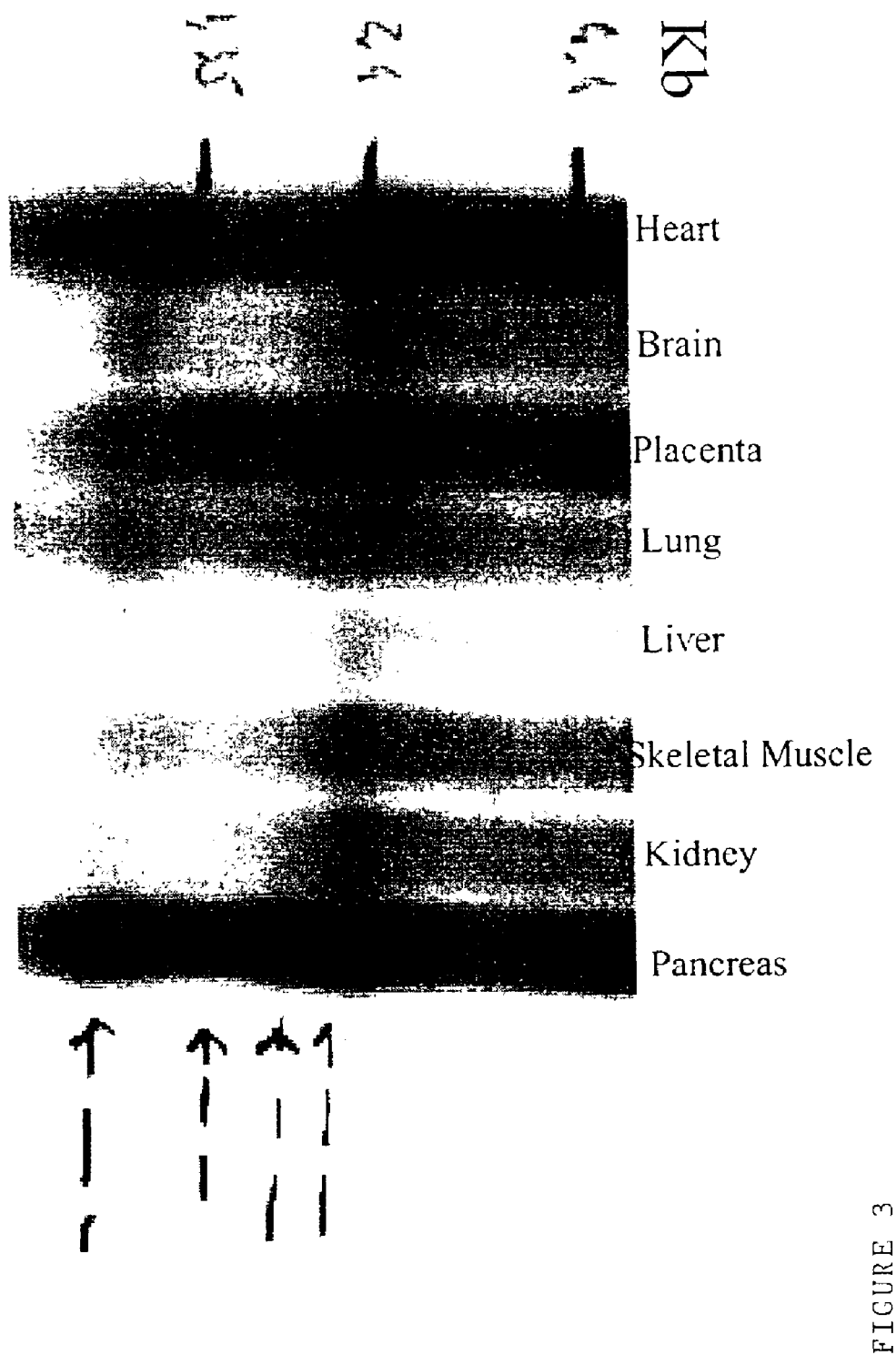
FIG. 3. Northern analysis of human tissues. The probe was the same as for FIG. 2.

MIF1 is expressed in a wide range of tissues, as tested by EST library screening. A Northern blot analysis of human tumor samples detects a sole messenger RNA of 2, 4 kb, expressed in all tested tumors (FIG. 2). MIF1 is also expressed in normal tissues as shown by Northern blot analysis of a normalized human multiple tissue blot (FIG. 3). A stronger expression was found in heart, pancreas and placenta, and in this last tissue different messengers could be detected. Observation of these different sized messengers indicates that natural splicing variants exist.

Figure 4:
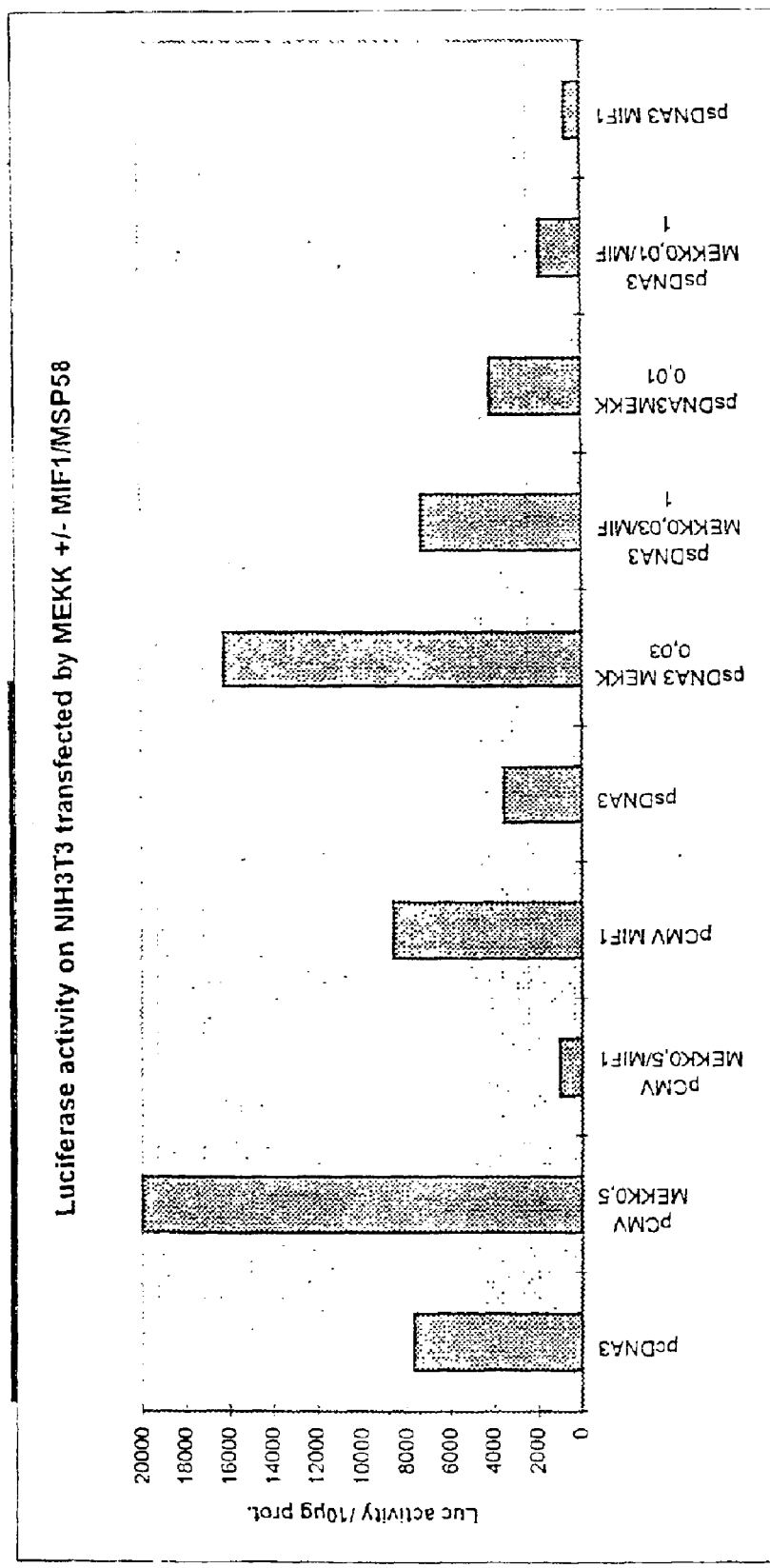
FIG. 4. Luciferase activity on NIH3 T3 cells transfected by MEKK with and without MIF1.

In transient transfection experiments in NIH3T3 cells, MIF1 protein decreased the level of JNK activation obtained by co-transfection with the MEKK1 protein fused with the Gal4 Jun reporter (FIG. 4). Stable transfectants were obtained in CHO and PC12 cells. No toxicity from overexpression of the MIF1 protein was observed. This is distinct from the catalytic domain of MEKK1, which has been reported to induce cell apoptosis when overexpressed in cells.

Figure 5:
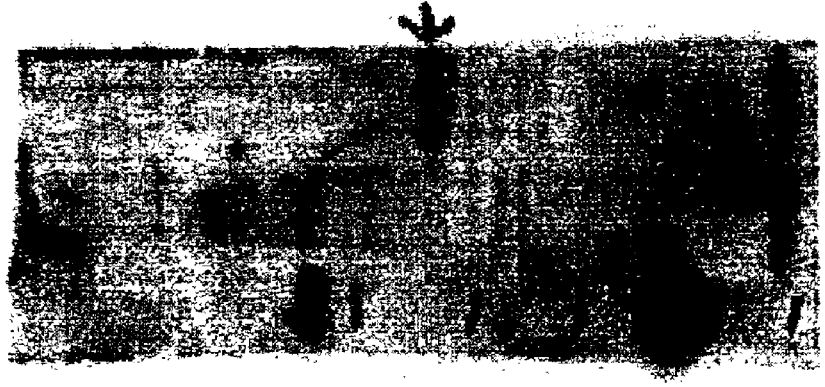
FIG. 5. Western blot of CHO K1 cellular extracts. Cells were transfected or not with pcDNA3 MIF1/MSP58 plasmid. MIF1 expression was determined by binding of a polyclonal antibody against peptide S14 Y (amino acid residues 16–28).

A polyclonal antibody directed against a peptide corresponding to amino acids 16–28 (S14Y) of MIF1 was generated. This antibody recognized both human and mouse MIF1 proteins and permitted MIF1 protein detection in Western blots (FIG. 5).

Example 13

Generation of Stable Clones Expressing MIF1 Protein

Figure 6:
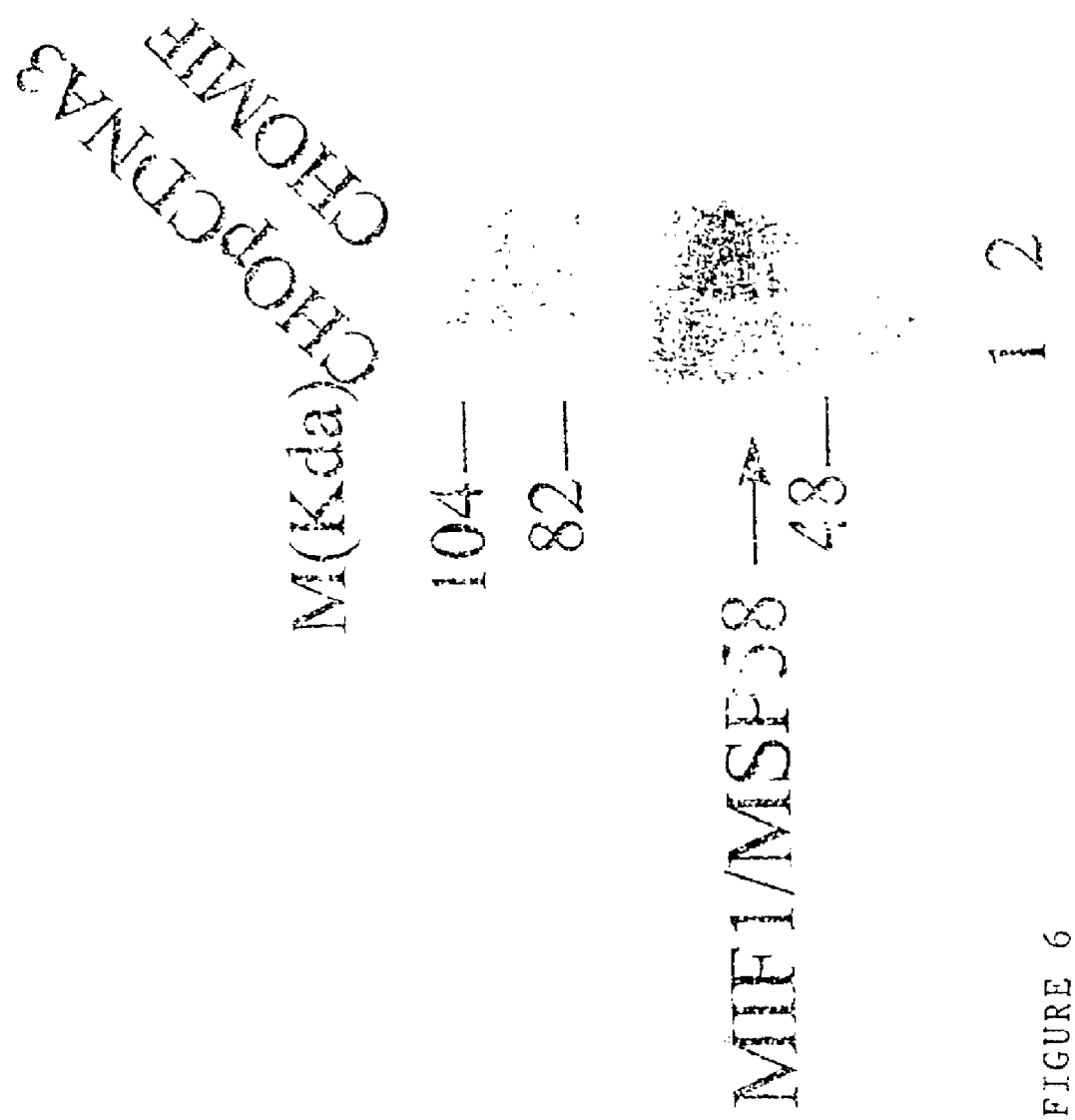
FIG. 6. Expression of MIF1 in CHO transfected cells (pool NeoR): CHOK1 were transfected with pcDNA3 (lane 1) and pCM562 (encoding for Myc-tagged MIF1/MSP58 protein) (lane 2) and selected with G418. Resistant cells were harvested and lysed. Cellular extracts were separated on 10% Tris-glycine PAGE-SDS, electro-blotted and expression of MIF1/MSP58 was detected using anti-myc antibody. Revelation was made using ECL system (Amersham) using secondary antibody coupled with peroxidase. MIF1/MSP58 protein was indicated by an arrow.
Figure 7:
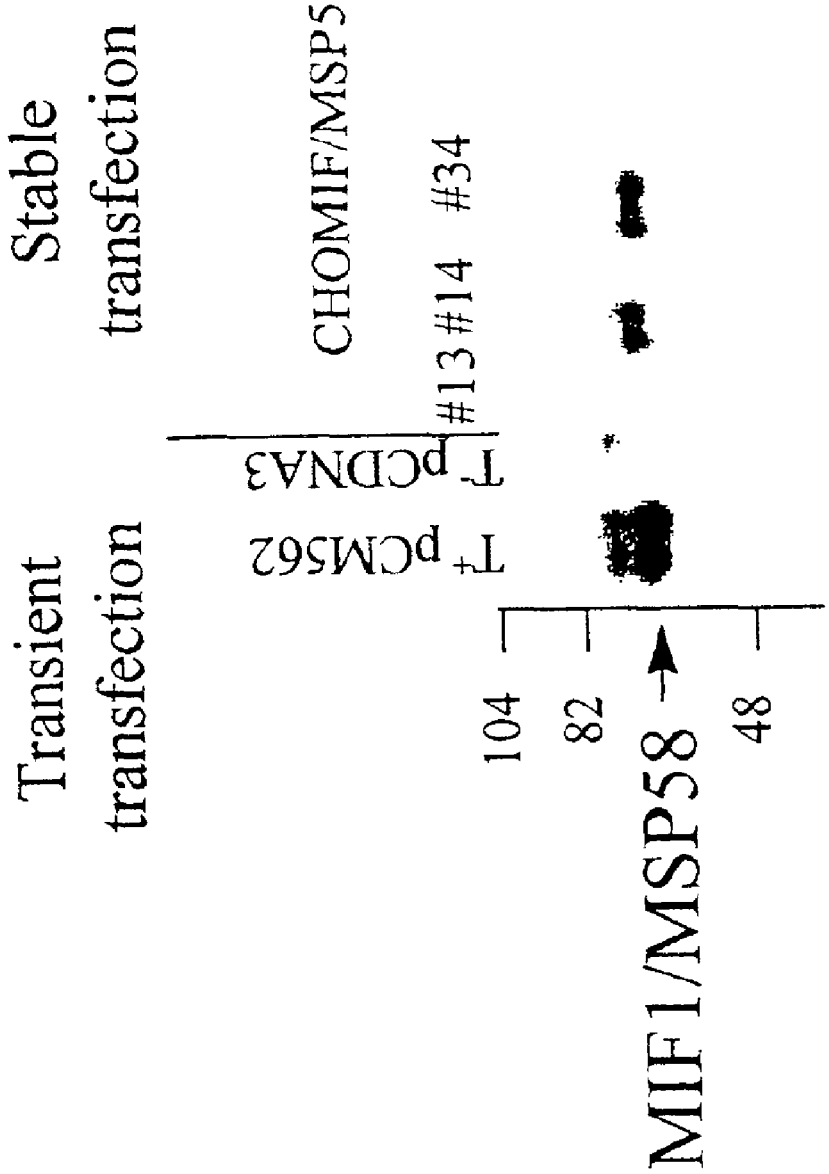
FIG. 7. Expression of MIF1 in stable clones: Individual stable clones were derived from a pool of NeoR resistant cells after transfection with pCM562 by limit-dilution of cellular suspension in 96-wells plates. After amplification, each clone (clones which are shown are #13, #14 and #34) was tested for MIF1/MSP58 protein expression using anti-myc antibody. Lane T+pCM562 was loaded with cellular extract of pool of transfected cells before cloning.
Figure 8:
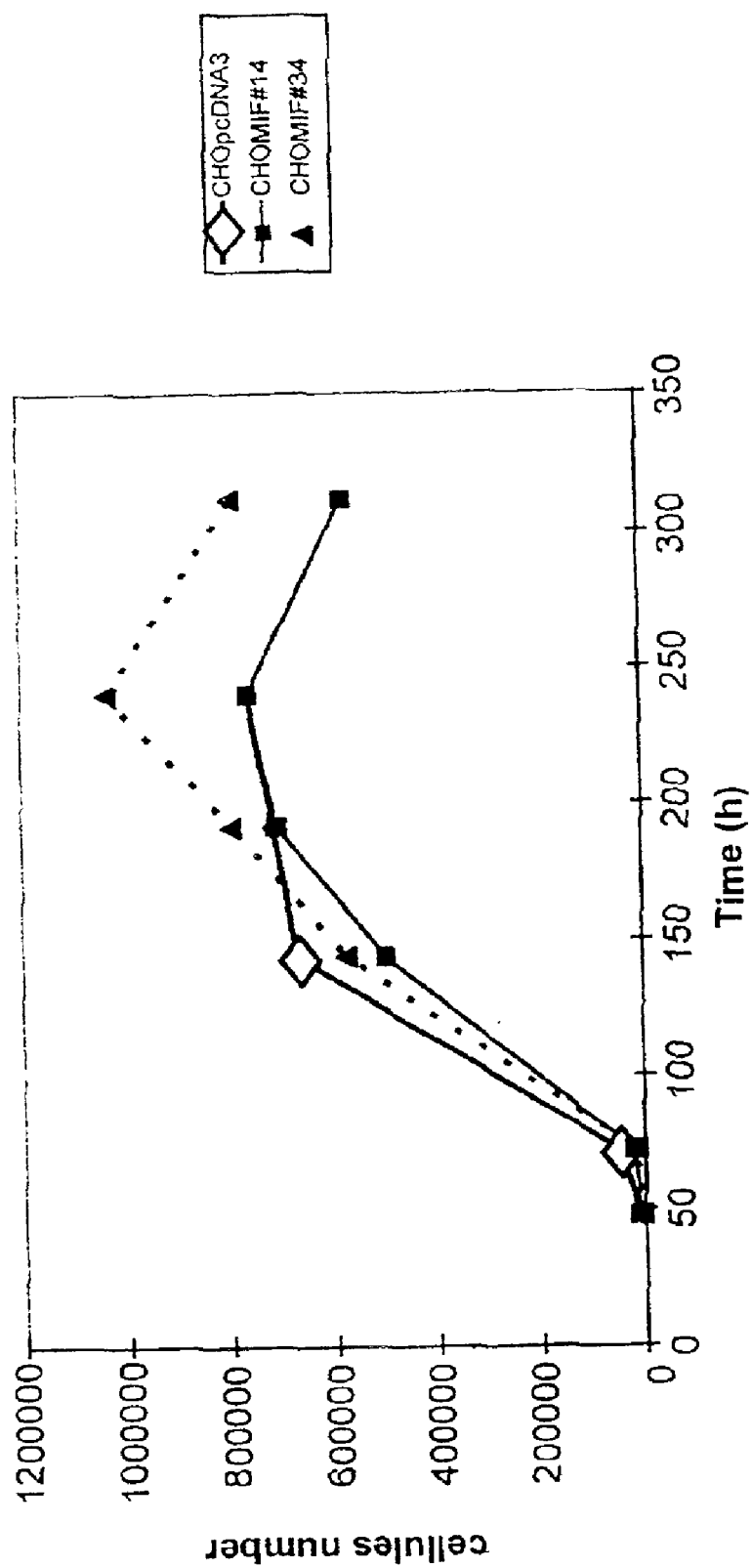
FIG. 8. Cells were seeded at a density of 1 at $5.10^3$ cells/well in a 24 well plate in complete medium (HAM's F12, 10% heat inactivated foetal bovine serum, 1% penicilline, 1% glutamine, 500 μG/mkl G418). At each time, well were numerated and results presented mean of 4 independent numeration.

Cells were transfected with plasmid encoding MIF1 cDNA under CMV promoter control (pCM562) or empty vector as a control (pcDNA3). Cellular extracts of pools of G418 resistant cells were analyzed by Western blot. Results showed that pCM562-stable transfected cells expressed the tagged-MIF1/MSP58 protein (FIG. 6). Analysis by immunofluorescence using anti-myc antibody showed unequal labelling of nucleus resulting in a variable level of expression of MIF1 protein in the pool of G418 resistant cells. Individual cloning of cell expressing high level of MIF1 protein was then realized and 36 individual clones were tested for MIF1 protein expression. Two clones were selected referring to high level of production of recombinant protein (#14 and #34) (FIG. 7). These clones did not showed significant difference in the growth rate compared to the control cells transfected with pcDNA3 vector (FIG. 8).

Example 14

MIF1 Inhibits JNK Activity Induced by Sorbitol

We used CHOMIF1 #34 to analyze the effect of MIF1 expression on activation of JNK through MEKK1 stimuli.

Figure 9:
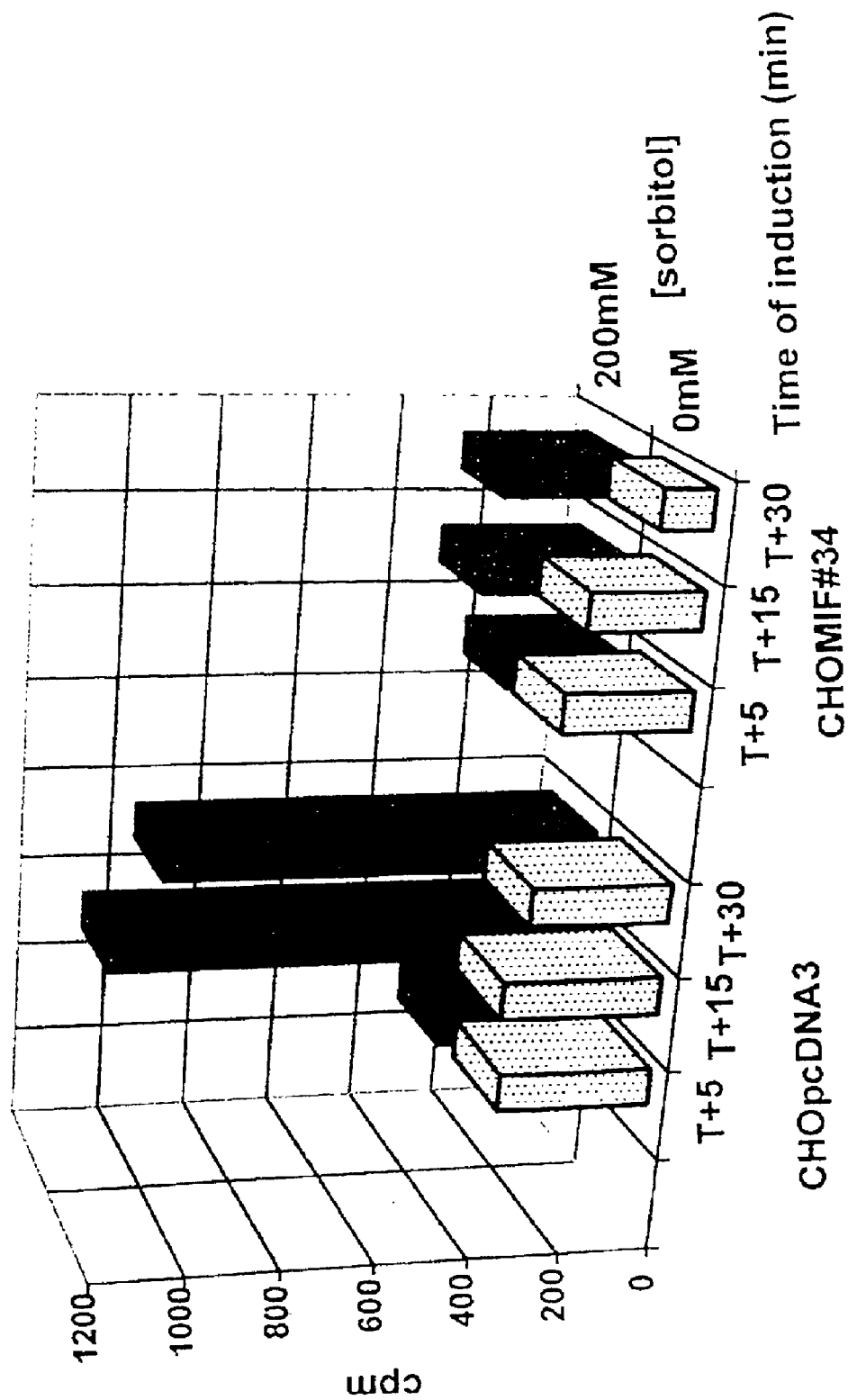
FIG. 9. MIF1/MSP58 inhibits JNK activity induced by sorbitol. The CHOpcDNA3 (CHO stable clone obtained with the empty vector) and CHO-MIF34 (CHO stable clone #34 overexpressing MIF1/MSP58) stable cells were stressed by Sorbitol (200 mM) during indicated times and the effect of MIF1/MSP58 overexpression on JNK activation was directly checked by phosphorylation of a GST-Jun (1–223) substrate by cytosolic extracts (in vitro phosphorylation).

Yuriji et al (Science (1998), vol 282, p 1911) showed that MEKK1 activates the JNKs in response to 200 mM sorbitol. In order to analyze the effect of MIF1 expression on activation of MEKK1 by sorbitol, we incubated CHOMIF1 cells and control cells (CHOpCDNA3) in presence of 200 mM of sorbitol for different times (5, 15 and 30 minutes). Cells extracts were then prepared and MEKK1 activation (and subsequent INK activation) was analyzed using in vitro GST-Jun (1–223) phosphorylation test (see Material and Methods). Cells expressing MIF1 showed an inhibition of JNK activation (revelated by weak GST-JUNphosphorylation) in response to sorbitol incubation (FIG. 9). These results indicated that MIF1 inhibited JNK activation following sorbitol (200 mM) stimuli apparently through MEKK1 activity inhibition.

Example 15

MIF1 Interacts with MEKK1 in Stress Conditions

Figure 11:
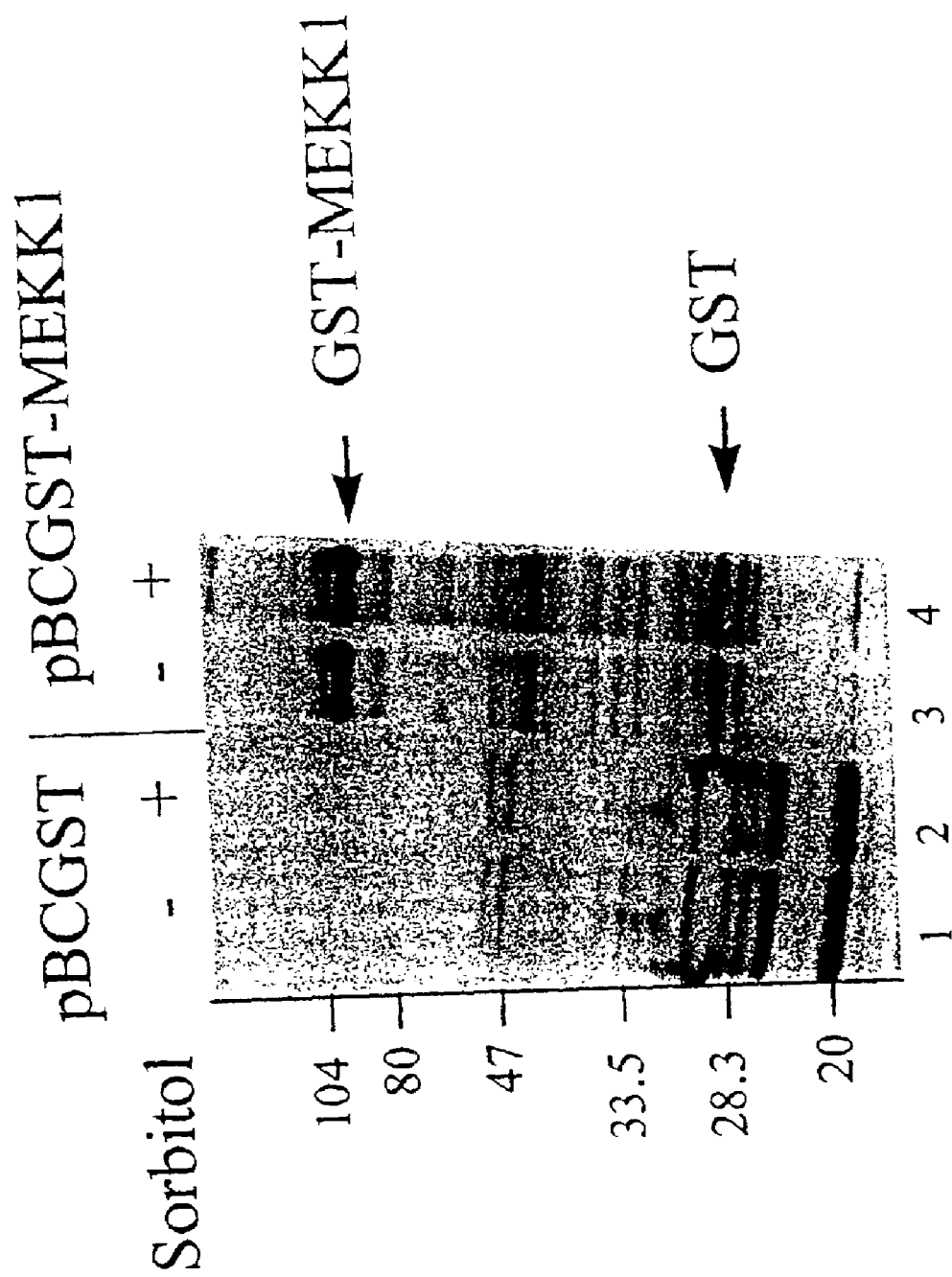
FIG. 11. GST-MEKK1 retention on GSH-sepharose. CHOMIF1/MSP58#34 cells were transfected with pBCGST (control vector, lane 1 and 2) or pBCGST-MEKK1 (lane 3 and 4) and treated (lane 1 and 3) or not (lane 2 and 4) with 200 mM sorbitol. Cellular extracts were fixed on GSH sepharose, and protein complexes were eluted with an excess of GSH. After loading on PAGE-SDS, bound proteins were analyzed using anti-GST antibody and reveled with ECL system. Results shown that both protein are bound on GSH-sepharose.
Figure 12:
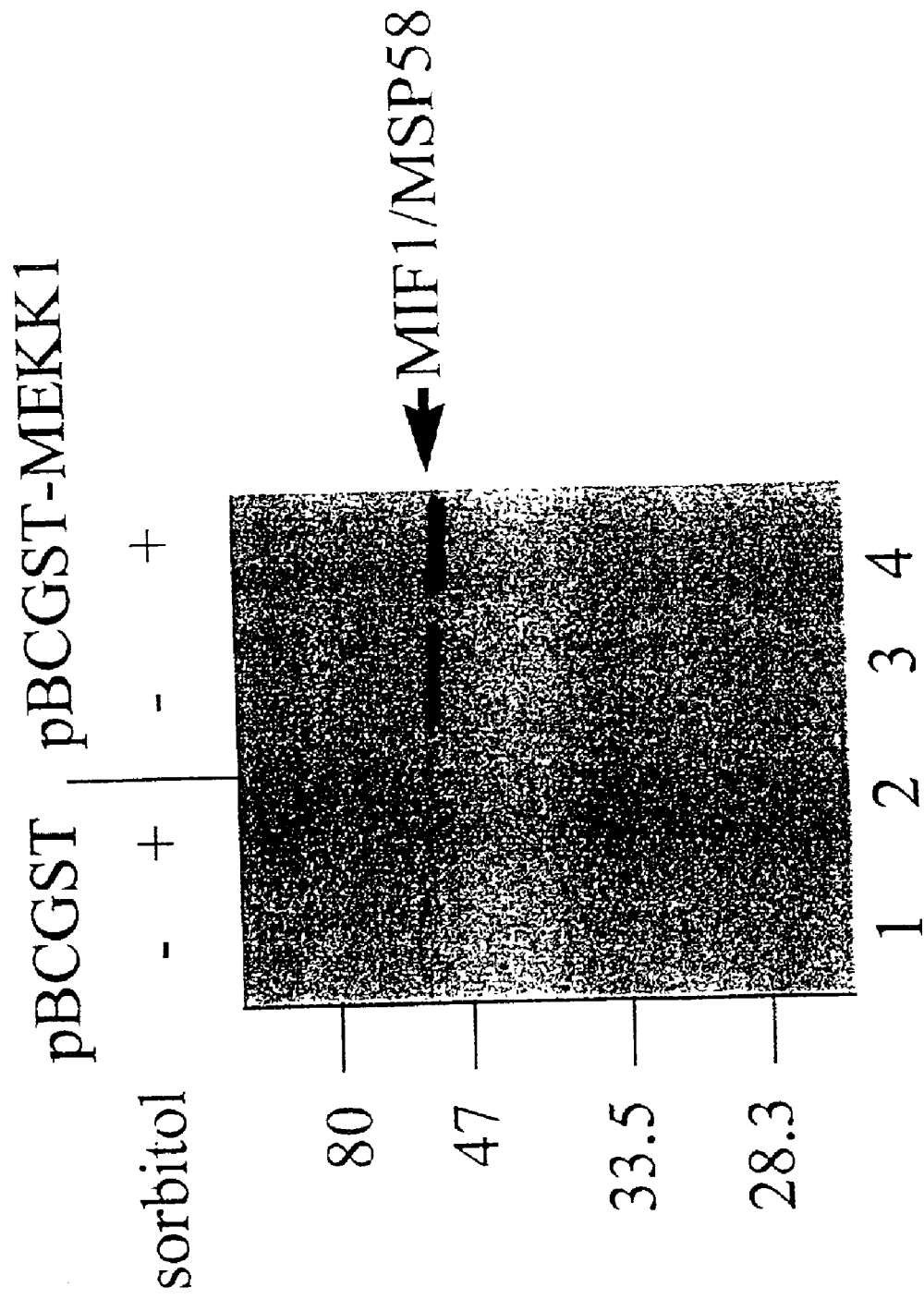
FIG. 12. GST pull-down indicates that MIF1/MSP58 interacts with MEKK1 protein. CHOMIF1/MSP58#34 cells were transfected with pBCGST (control vector, lane 1 and 2) or pBCGST-MEKK1 (lane 3 and 4) and treated (lane 1 and 3) or not (lane 2 and 4) with 200 mM sorbitol. Cellular extracts were fixed on GSH sepharose, and bound proteins were eluted with GSH. After loading on PAGE-SDS, MIF1-MSP58 presence was detected by using an anti-myc antibody and reveled with ECL system. Results indicate that MIF1/MSP58 binds to GST-MEKK1 and that the binding is regulated by stress.

In order to analyze the interaction between MEKK1 protein and MIF1 protein in cells, we constructed a recombinant plasmid which encodes for GST-MEKK1 protein (around 120 Kda) (see Material and Methods). After transfection in CHOMIF1 #34 cells, sorbitol (200 mM) was added or not during 30 min, cells were then lyzed and GST-proteins were fixed on GSH-sepharose. After elution with an excess of GSH solution, protein complexes were separated onto Tris-Glycine PAGE-SDS and analyzed by Western Blot using anti-GST antibody (FIG. 11) or anti-myc antibody (FIG. 12). Results presented in FIG. 11 indicated that GST and GST-MEKK 1 interacted with GSH sepharose after incubation of cellular extracts. FIG. 12 showed that MIF1-myc-tagged cellular protein interacted with MEKK1 protein. This interaction is more important in stress conditions (+sorbitol) (compare lane 4 to 3), indicating that MIF1-MEKK1 interaction is facilitated by MEKK1 phosphorylation as previously shwown in yeast 2-hybrid experiments. These results confirm data obtained in 2-hybrid yeast system and indicated that MIF1 protein interacts in cells with phosphorylated MEKK1 protein.

Taken together, these results validate the capacity of MIF1 to inhibit the activity of stress kinase cascade by MEKK1 protein and that occurs by direct interaction with MEKK1 protein.

Example 16

MIF1 Enhances Sensitivity of Cells to Apoptosis by Inhibiting MEKK1 Activity It was shown that activation of MEKK1 could protect from cell apoptosis due to long term exposure to sorbitol (Yuriji et al, (1998), Science vol 282, p1911; Yuriji et al (1999), J. Biol. Chem., vol 274, p12605).

Figure 10:
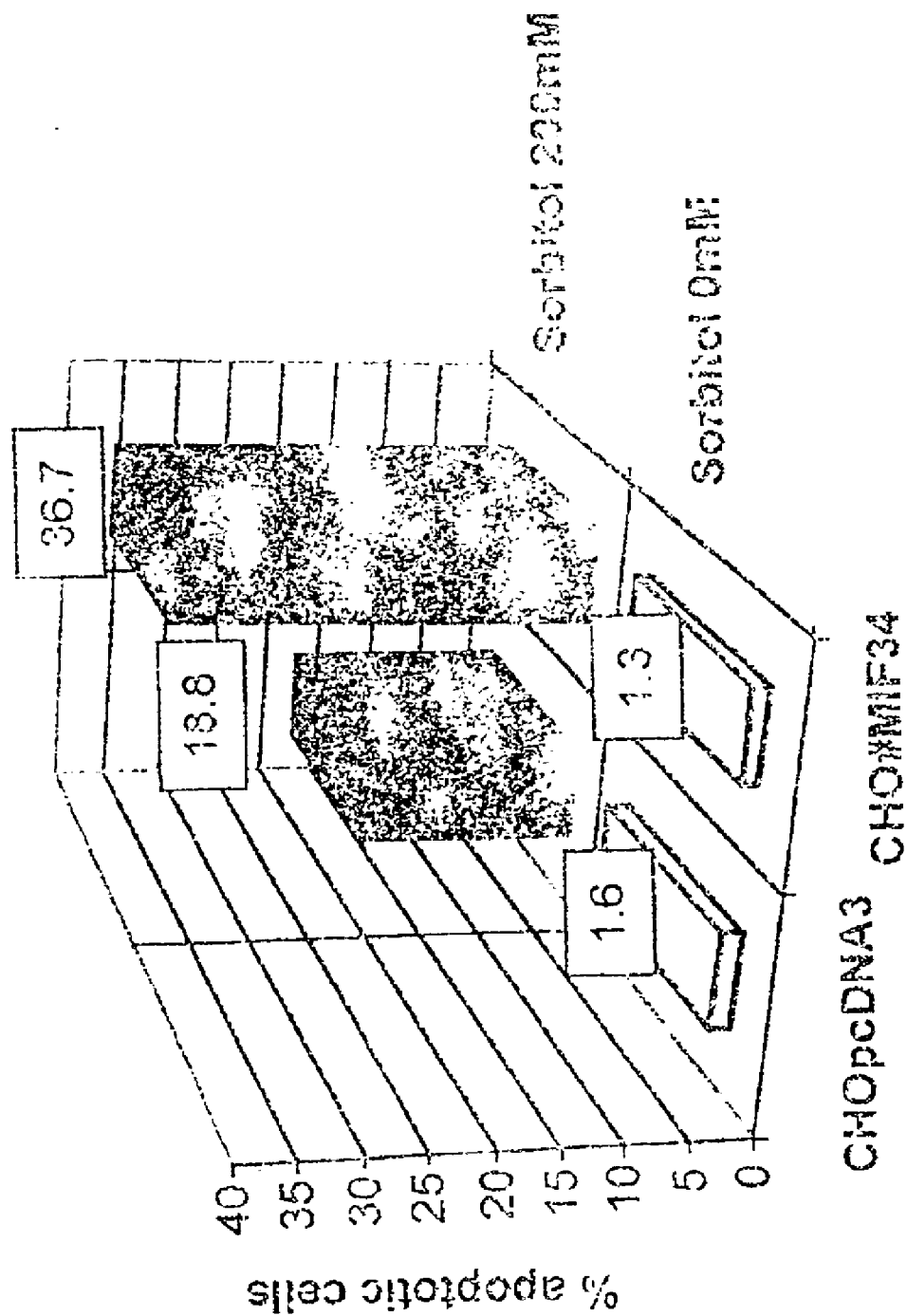
FIG. 10. MIF1/MSP58 expression increases apoptosis in response to a mild osmotic shock (200 mM sorbitol). Cells were seeded in 6-well plate and incubated 24 h with or whithout 200 mM sorbitol. Apoptosis was then detected by FACS after propidium iodure staining.

The sensitivity to apoptosis of CHOpCDNA3 and CHOMIF1 #34 was analyzed after incubation of cells 24 h in 200 mM sorbitol. Results indicated that cells which expressed MIF1 are more sensitive to sorbitol induced apoptosis than control cells (FIG. 10).

Example 17

Test for Identification of Compounds Able to Disrupt MEKK1-MIF1 Protein Interaction The method described here allows for the identification of drug(s) inhibiting the MEKK1-MIF1 interaction, as well as the kinase activity f MEKK1. This method is based on 2 hybrid technology (reviewed in Fields S, Sternglanz R Trends Genet 1994 August; 10(8):286–92 The two-hybrid system: an assay for protein—protein interactions/Mendelsohn A R, Brent R Curr Opin Biotechnol 1994 October; 5(5):482–6 Applications of interaction traps/two-hybrid systems to biotechnology research/Bemis L T, Geske F J, Strange R. Methods Cell Biol 1995;46:139–51 Use of the yeast two-hybrid system for identifying the cascade of protein interactions resulting in apoptotic cell death/White M A. Proc Natl Acad Sci USA 1996 September 17; 93(19):10001–3 The yeast two-hybrid system: forward and reverse/Luban J, Goff S P Curr Opin Biotechnol 1995 February; 6(1):59–64 The yeast two-hybrid system for studying protein—protein interactions./Bai C, Elledge S J Methods Enzymol 1996;273:331–47 Gene identification using the yeast two-hybrid system/Frederickson R M Curr Opin Biotechnol 1998 February; 9(1): 90–6 Macromolecular matchmaking: advances in two-hybrid and related technologies./T Colas P, Brent R rends Biotechnol 1998 August; 16(8):355–63 The impact of one-hybrid and related methods on biotechnology./Vidal M, Legrain P Nucleic Acids Res 1999 February 15;27(4):919–29 Yeast forward and reverse 'n'-hybrid systems.).

Full length MEKK1 or deleted MEKK1 fused to a DNA binding domain are used (corresponding coding sequences are cloned in yeast plasmids pCM433 and pCM486 as example (described in example 1 and 4)). Full length MIF1 or deleted MIF1 fused to a transactivator domain is used (as example corresponding coding sequence are cloned in plasmids PCM480 (described in example 3). Yeast two hybrid strains used have at least one reporter gene (among them URA3, HIS3, LEU2, CYH2, CAN1, lacz, GFP or other reporter genes) and associated mutation(s) allowing the detection of a gene reporter expression (i.e ura3 mutation if URA3 gene is used as reporter gene etc. . . ) with or without additional gene mutation(s) or inactivation(s) in order to increase the internal concentration of each compound tested (see WO96/10082). As an example yeast yCM17 strain described in materiel et methods is used. Drugs which lead to a decrease of MEKK1/MIF1 interaction induce a decrease of gene reporter(s) expression. Different methods can be used to monitored the expression of the gene reporter such as colorimetric/.fluorometric/luminescent enzymatic assays of the enzymatic protein encoded by gene(s) reporter, —growth inhibition halo can be measured on medium selective for gene reporter complementing a yeast chromosomal mutation versus unselective medium, growth halo determination when a counter-selection is available (fluoorate containing medium if the reporter gene is URA3, canavanine containing medium for CAN1 as reporter gene with a yeast harboring a can1 mutation or inactivation etc. . . ). All these methods used in yeast biology are well are widely described in litterature (Methods Enzymol 1991; 194:1–863 Guide to yeast genetics and molecular biology, Methods Enzymol 1983, 101:167–346 Recombinant DNA, Biotechnology 1989; 13:1–354 Yeast genetic engineering; Methods in molecular biology 1996, 53, 1–433 Yeast protocols; Molecular Genetics of Yeast: A Practical Approach Edited by John R. Johnston 1994 1–300; The Yeast Two-Hybrid System 1997 1–356 Paul L. Bartel, and Stanley Fields; Methods in Yeast Genetics: A Laboratory Course Manual 1997; Methods in Yeast Genetics: A Laboratory Course Manual, 1990).

Figure 13:
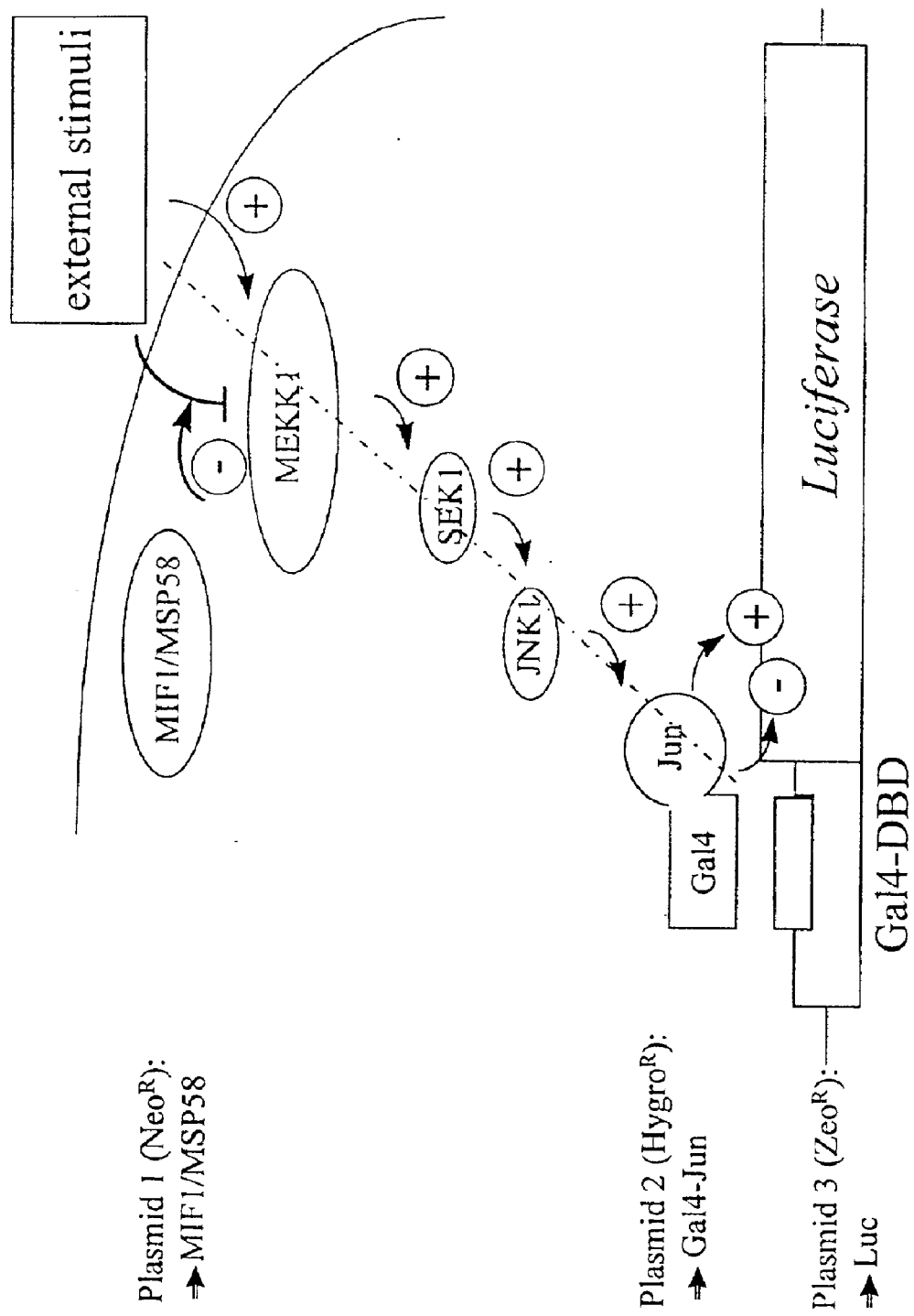
FIG. 13. Principle of secondary screen for identification of antagonists or agonists of MIF1/MSP58-MEKK1 binding.

The principle of secondary screen to identify antagonists or agonists of MIF1/MSP58-MEKK1 binding is described in FIG. 13. A cellular stable clone over-expressing the MIF1/MSP58 (clone CHOMIF #34 for example) is transfected with a reporter system reflecting the activation of MEKK1/JNK pathway (Yujiri et al, 1999, J. Biol. Chem. Vol 274, p12605; Yujiri et al, 1998, Science, vol 282, p1911). The plasmid 1 codes for MIF1/MSP58 (pCM562 as example) and carries the Neomycine resistance gene. Plasmid 2 and 3 provides for the reporter gene system Gal4-Jun/Gal 4 Luc (Lassignal Johnson et al, 1996 J. Biol. Chem. Vol 271, p 3229; Gupta et al, 1993, Proc. Natl. Acad. Sci. Vol 90, p3216; Hibi et al 1993, Genes and Dev., Vol 7, p2135) and carry two other different selectable markers (plasmid 2 carries for example the hygromycine resistance gene and plasmid 3 carries Zeocine resistance gene). The plasmid 2 encodes for the fusion protein $Gal4_{(1-147)}$–$Jun_{(1-233)}$ (Hibi et al 1993, Genes and Dev., vol 7, p2135, Sadowski et al, 1989, Nucleic Acids Res, Vol 17, p7539). This protein can bind the Gal4-DBD sequence located in the promoter upstream the reporter gene luciferase (Gupta et al, 1993, Proc. Natl. Acad. Sci. Vol 90, p3216) and activates the transcription of Luciferase gene if Jun part is phosphorylated. The external stimuli to activate the MEKK1/JNK pathway can be low concentration of sorbitol (200 mM) or cold shock or nocodazole (0.5 μg/ml) or other (Yujiri et al, 1999, J. Biol. Chem. Vol 274, p12605; Yujiri et al, 1998, Science, vol 282, p1911). Molecules to be tested are added in the complete medium in presence (or before or after) the external stimuli. Luciferase activity is analyzed after cell lysis according to the manufacturer's instructions (Promega) and measured with a luminometer.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated nucleic acid encoding an MEKK interacting forkhead associated (FHA) protein that comprises the amino acid sequence of SEQ ID NO:2.

2. The isolated nucleic acid of claim 1 comprising the nucleotide sequence as depicted in SEQ ID NO:1.

3. The isolated nucleic acid of claim 1, further comprising a sequence encoding a polypeptide tag, whereby the nucleic acid encodes a chimeric tagged MEKK interacting FHA protein.

4. A vector comprising the isolated nucleic acid of claim 1.

5. The vector according to claim 4 wherein the isolated nucleic acid is operatively associated with an expression control sequence permitting expression of the MEKK interacting FHA protein in an expression competent host cell.

6. The vector according to claim 5 selected from the group consisting of an RNA molecule, a plasmid DNA molecule, and a viral vector.

7. A composition comprising the plasmid DNA molecule of claim 6 and a DNA condensing protein, a cationic lipid, a liposome, a polymer, or a DNA precipitating agent.

8. The viral vector according to claim 6, selected from the group consisting of a retrovirus, an adenovirus, an adeno-associated virus, a herpes virus, and an vaccinia virus.

9. A host cell transfected with the vector of claim 4.

10. A host cell transfected with the vector of claim 5.

11. The host cell of claim 10 selected from the group consisting of a bacterial cell, a yeast cell, and a mammalian cell.

12. A method for producing an MEKK interacting forkhead associated (FHA) protein comprising the amino acid sequence of SEQ ID NO:2, comprising:

culturing the host cell of claim 10 in culture medium under conditions permitting expression of the MEKK interacting FHA protein; and isolating the the MEKK interacting FHA protein from the culture.

13. An isolated MEKK interacting forkhead associated (FHA) protein comprising the amino acid sequence of SEQ ID NO:2.

14. The isolated MEKK interacting FHA protein of claim 13, further comprising a polypeptide tag.

15. A vector comprising the isolated nucleic acid of claim 2.

16. The vector according to claim 15, wherein the isolated nucleic acid is operatively associated with an expression control sequence.

17. The vector of claim 16, selected from the group consisting of an RNA molecule, a plasmid DNA molecule, and a viral vector.

18. A composition comprising the plasmid DNA molecule of claim 17 and a DNA condensing protein, a cationic lipid, a liposome, a polymer, or a DNA precipitating agent.

19. The viral vector according to claim 17, selected from the group consisting of a retrovirus, an adenovirus, an adeno-associated virus, a herpes virus, and a vaccinia virus.

20. A host cell transfected with the vector of claim 15.

21. A host cell transfected with the vector of claim 16.

22. The host cell of claim 21 selected from the group consisting of a bacterial cell, a yeast cell, and a mammalian cell.

23. A method for producing MEKK interacting forkhead associated (FHA) protein comprising the amino acid sequence of SEQ ID NO:2, comprising:

culturing the host cell of claim 21 in culture medium under conditions permitting expression of the MEKK interacting FHA protein; and isolating the the MEKK interacting FHA protein from the culture.

\* \* \* \* \*